United States Patent [19]
de Meijere et al.

[11] Patent Number: 5,407,599
[45] Date of Patent: Apr. 18, 1995

[54] CYCLOPROPYLAKLYL OR -ALKENYL OR HETEROCYCLIC COMPOUNDS, PROCESS FOR THEIR PREPARATION AND THEIR USE IN LIQUID-CRYSTALLINE MIXTURES

[75] Inventors: Armin de Meijere, Seevetal; Hans-Rolf Dübal, Königstein/Taunus; Claus Escher, Mühltal; Wolfgang Hemmerling, Sulzbach; Ingrid Müller, Hofheim am Taunus; Dieter Ohlendorf, Liederbach; Rainer Wingen, Hattersheim am Main; Takamasa Harada; Gerhard Illian, both of Frankfurt am Main, all of Germany; Mikio Murakami, Kakegawa, Japan

[73] Assignee: Hoechst Aktiengesellschaft, Frankfurt am Main, Germany

[21] Appl. No.: 131,763
[22] Filed: Oct. 4, 1993

Related U.S. Application Data

[63] Continuation-in-part of Ser. No. 917,792, Jul. 20, 1992, abandoned, and Ser. No. 919,085, Jul. 23, 1992, abandoned, which is a continuation of Ser. No. 799,754, Nov. 27, 1991, abandoned, which is a continuation of Ser. No. 522,248, May 11, 1990, abandoned, said Ser. No. 917,792, is a continuation of Ser. No. 804,618, Dec. 4, 1991, abandoned, which is a continuation of Ser. No. 560,017, Jul. 27, 1990, abandoned, which is a continuation of Ser. No. 275,210, Nov. 23, 1988, abandoned.

[30] Foreign Application Priority Data

Nov. 25, 1987 [DE] Germany ............... 37 39 884.9
May 13, 1989 [DE] Germany ............... 39 15 804.7

[51] Int. Cl.⁶ ............... C09K 19/52; C09K 19/34; C07D 239/26
[52] U.S. Cl. ............... 252/299.01; 252/299.61; 252/299.63; 252/299.64; 252/299.65; 252/299.67; 544/229; 544/242; 544/298; 544/335
[58] Field of Search ............... 252/299.01, 299.61, 252/299.63, 299.64, 299.65, 299.66, 299.67; 544/298, 242, 335, 229; 359/103, 104

[56] References Cited

U.S. PATENT DOCUMENTS

| | | |
|---|---|---|
| 3,948,961 | 4/1976 | Henrick et al. ............... 560/1 |
| 3,966,969 | 6/1976 | Willy et al. ............... 424/343 |
| 4,014,922 | 3/1977 | Henrick et al. ............... 560/1 |
| 4,638,073 | 1/1987 | Welba et al. ............... 549/556 |
| 4,820,839 | 4/1989 | Krause et al. ............... 544/316 |
| 4,876,028 | 10/1989 | Hemmerling et al. ......... 252/299.61 |
| 4,880,561 | 11/1989 | Tabohashi et al. ............. 252/299.61 |
| 4,927,244 | 5/1990 | Bahr et al. ............... 359/103 |
| 5,200,521 | 4/1993 | Illian et al. ............... 544/298 |

FOREIGN PATENT DOCUMENTS

| | | |
|---|---|---|
| 0104011 | 3/1984 | European Pat. Off. |
| 244129 | 11/1987 | European Pat. Off. |
| 0289270 | 11/1988 | European Pat. Off. |
| 0316181 | 5/1989 | European Pat. Off. |
| 318423 | 5/1989 | European Pat. Off. |
| 0318423 | 5/1989 | European Pat. Off. |
| 0343487 | 11/9189 | European Pat. Off. |
| 3633968 | 10/1986 | Germany . |
| 2-118618 | 5/1990 | Japan . |

OTHER PUBLICATIONS

Shobara et al., Chemical Abstracts, vol. 113, No. 26 (Dec. 26, 1990), Abstract No. 241609.

Primary Examiner—Shean Wu
Attorney, Agent, or Firm—Curtis, Morris & Safford

[57] ABSTRACT

Disclosed and claimed are liquid-crystalline cyclopropylalkyl or -alkenyl or heterocyclic compounds, process for their preparation, and their use in liquid-crystalline mixtures. The novel cyclopropylalkyl or -alkenyl or heterocyclic compounds are of the general formula

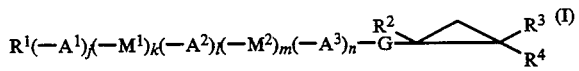

In this formula $A^1$, $A^2$ and $A^3$ are unsubstituted or substituted, aromatic or heteroaromatic molecular components such as 1,4-phenylene or pyrimidine-2,5-diyl which are linked via a single bond (in the case where k and m=0) or via functional groups $M^1$ and $M^2$, such as CO—O or $CH_2$—O; j, k, l, m and n are zero, 1 or 2. The radicals $R^2$, $R^3$ and $R^4$ are H or alkyl/alkenyl, $R^1$ is alkyl/alkenyl or one of the substitutents known from LC chemistry such as an α-haloalkanoic acid radical. At least one of the components $A^1$, $A^2$ and $A^3$ can be heteroaromatic, and G is alkylene or alkenylene.

19 Claims, No Drawings

CYCLOPROPYLAKLYL OR -ALKENYL OR HETEROCYCLIC COMPOUNDS, PROCESS FOR THEIR PREPARATION AND THEIR USE IN LIQUID-CRYSTALLINE MIXTURES

RELATED APPLICATIONS

This application is a continuation-in-part of application Ser. No. 07/919,085, filed Jul. 23, 1992, now abandoned, which in turn is a continuation of application Serial No. 07/799,754, filed Nov. 27, 1991, now abandoned, which in turn is a continuation of application Ser. No. 07/522,248, filed May 11, 1990, now abandoned, with a claim of priority from German application No. P3915804.7, filed May 13, 1989; each of these predecessor U.S. and priority German applications are hereby incorporated herein by reference. This application is also a continuation-in-part of application Ser. No. 07/917,792, filed Jul. 20, 1992, now abandoned, as a continuation of application Ser. No. 07/804,618, filed Dec. 4, 1991, now abandoned, as a continuation of application Ser. No. 07/560,017, filed Jul. 27, 1990, now abandoned, as a continuation of application Serial No. 07/275,210, filed Nov. 23, 1988, now abandoned, with a claim of priority from German application No. P3739884.9, filed Nov. 25, 1987; and, each of these predecessor U.S. and priority German applications are hereby incorporated herein by reference. This application claims the benefits of priority under 35 U.S.C. §119 from German applications P3915804.7 and P3739884.9, filed respectively on May 13, 1989 and Nov. 25, 1987.

FIELD OF THE INVENTION

The present invention relates to cyclopropylalkyl or -alkenyl or heterocyclic compounds, processes for their preparation and their use in liquid-crystalline mixtures.

BACKGROUND OF THE INVENTION

The unusual combination of anisotropic and fluid behaviour of liquid crystals has resulted in their use in a large number of electro-optical switching and display devices. In these, their electrical, magnetic, elastic and/or thermal properties can be used for changes in orientation. Optical effects can then be achieved, for example, with the aid of birefringence, the inclusion of dichroically absorbing dye molecules ("guest-host mode") or light scattering.

In order to satisfy the constantly increasing practical requirements in the various fields of application, there is a constant demand for novel, improved liquid-crystal mixtures and thus also for a large number of mesogenic compounds of a very wide variety of structures. This applies both to the areas in which nematic LC phases (for example TN="twisted nematic", STN="supertwisted nematic", SBE="supertwisted birefringence effect", ECB="electrically controlled birefringence") are used, and in those using smectic LC phases (for example ferroelectric and electroclinic).

Many of the compounds which are suitable for LC mixtures can be described by a structure principle (building plan) [see, for example J. Am. Chem. Soc. 108, 4736 (1986), structure I; Science 231, 350 (1986), FIG. 1A; J. Am. Chem. Soc. 108, 5210 (1986), FIG. 3] in which nuclei of cyclic compounds—aromatics, heteroaromatics, but also saturated ring systems—are linked to alkyl side chains which are straight-chain or substituted in the chain by small groups (for example methyl or chlorine) and are thus branched.

Compounds which contain a terminal cyclopropyl-substituted alkyl chain as a partial structural element are described, for example, in U.S. application Nos. 3,948,961, 3,966,969 and 4,014,922 (Henrick et al.). The compounds are said to be suitable as insecticides, but a liquid-crystalline behaviour is not reported. The compounds listed in these publications differ from those defined below, in particular through the fact that they are always linked to the molecular radical via an ester function and in this molecular radical, although having aromatic ring systems, do not contain any heteroaromatic ring systems.

EP-A 0,244,129 relates to 2,2-dimethylcyclopropane derivatives which are optically active and are linked to one of the known mesogenic radicals via a —CO—O—CH$_2$—, —O—CO— or —CH$_2$— bridge (the cyclopropyl ring is located at the right-hand end of the particular bridging member). These compounds are said to be suitable as components for ferroelectric LC mixtures (spontaneous polarization of up to 11 nC/cm$^2$).

OBJECTS AND SUMMARY OF THE INVENTION

The object of the present invention is to provide novel mesogenic compounds which can be combined with many other components to form a very wide variety of LC mixtures. The compounds defined below achieve this object:

Liquid-crystalline cyclopropylalkyl or -alkenyl and/or heterocyclic compounds of the general formula (I)

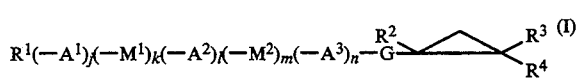

in which:

R$^1$ is straight-chain or branched (with or without an asymmetrical carbon atom) alkyl or alkenyl having 2 to 16 carbon atoms, it also being possible for one or two non-adjacent —Ch$_2$— groups to be replaced by —O—, —S—, —CO—, —CO—O—, —O—CO— or —O—CO—O and it also being possible for H to be replaced by F, or one of the following radicals

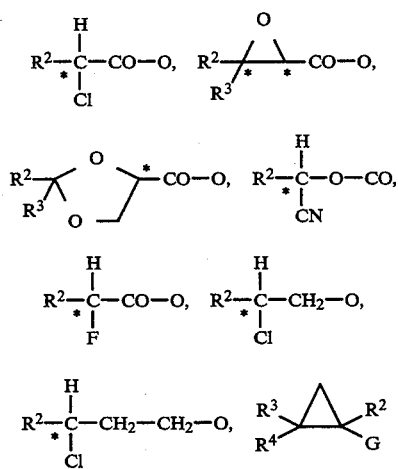

CN, OCF$_3$, OCF$_2$, F or CF$_3$; A$^1$, A$^2$, and A$^3$ are identical or different, unsubstituted or mono-or dihalo-substituted 1,4-phenylene, unsubstituted or 1- or 4-CN-substituted 1,4-cyclohexylene, trans-1,4-cyclohexene, pyrazine-2,5-diyl, pyridazine-3,6-diyl, pyridine-2,5-diyl, pyrimidine-2,5-diyl, or (1,3,4)-thiadiazole-2,5-diyl;

$M^1$ and $M^2$ are identical or different CO—O, O—CO, CO—S, S—CO, CH$_2$—O, O—CH$_2$, C≡C, CH$_2$—CH$_2$ or a single bond;

G is a straight-chain or branched alkylene having 1 to 16 carbon atoms or alkenylene having 2 to 16 carbon atoms in which it is also possible for one or two non-adjacent —CH$_2$— groups to be replaced by —O—, —S—, —O—CO—, —CO—O—, —S—CO— or —CO—S—;

$R^2$, $R^3$ and $R^4$ are H or straight-chain or branched alkyl having 1 to 16 carbon atoms or alkenyl having 2 to 16 carbon atoms in which it is also possible for one —CH$_2$— group to be replaced by —O—, —CO—O— or —O—CO—;

k and m are zero or 1; and j, l and n are zero, 1 or 2.

In some instances it is preferred that: a) j+l+n=2 or 3; and/or b) one of the groups $A^1$, $A^2$ and $A^3$ is not 1,4-phenylene or trans-1,4-cyclohexylene; and/or c), in the case where $R^2$=H, $R^3$ and $R^4$ need not simultaneously be CH$_3$ and G need not be CO—O—CH$_2$, O—CO or OCH$_2$, more preferably $R^3$ and $R^4$ are not simultaneously CH$_3$.

DETAILED DESCRIPTION

Preferred compounds of this type are those in which, in the general formula (I), the $(—A^1)_j(—M^1)_k(—A^2)_l(—M^2)_m(—A^3)_n—$ group denotes:

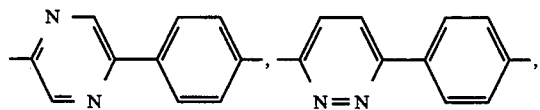

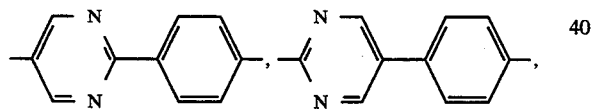

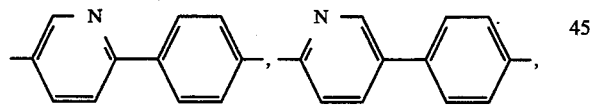

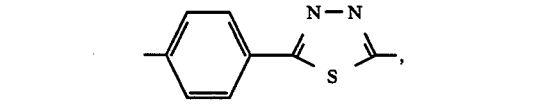

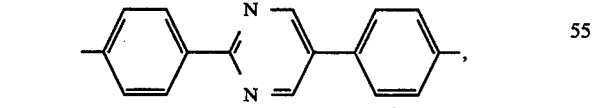

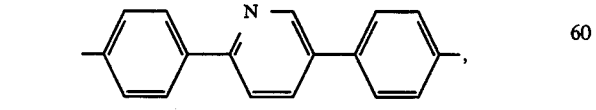

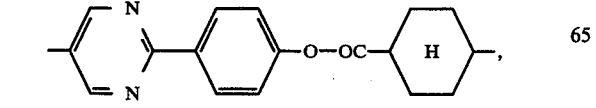

-continued

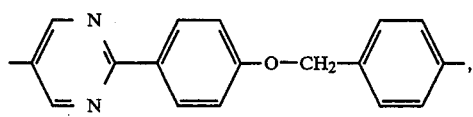

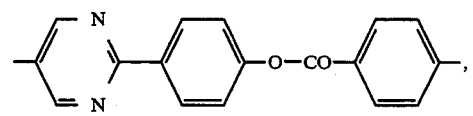

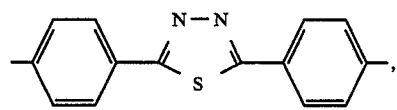

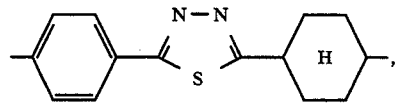

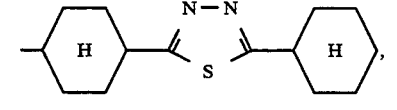

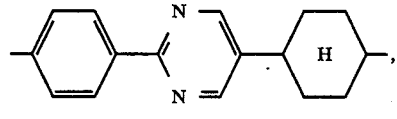

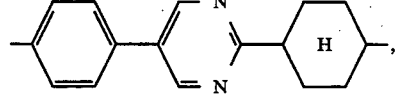

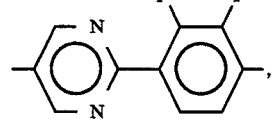

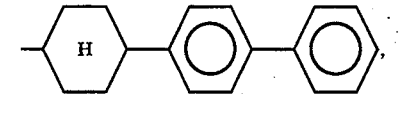

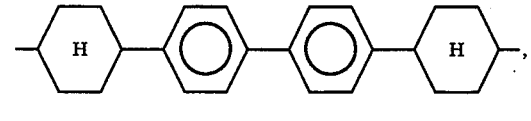

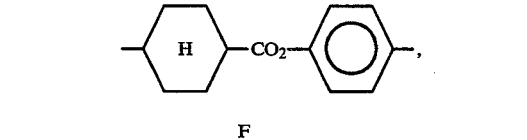

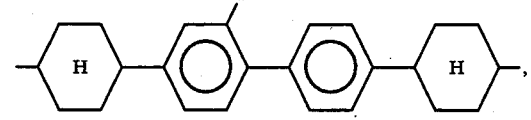

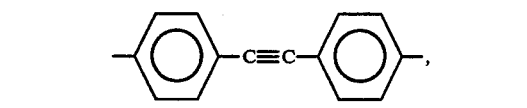

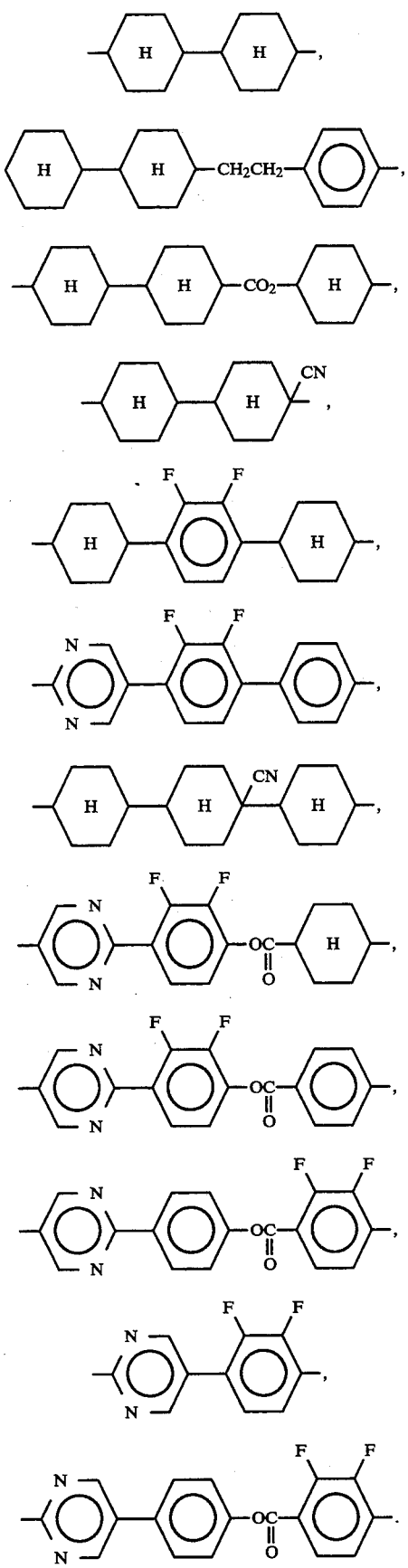
In addition, particularly preferred compounds are those in which, in the general formula (I), the group $R^1(-A^1)_j(-M^1)_k(-A^2)_l(-M^2)_m(-A^3)_n$ is:
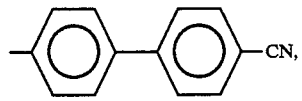
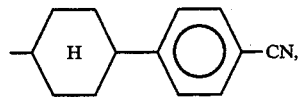
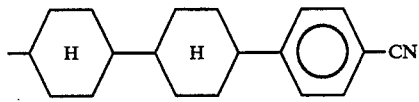
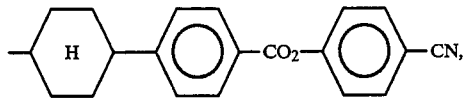
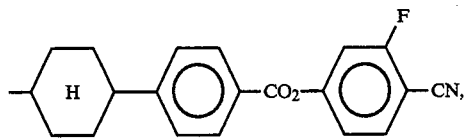
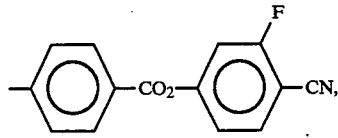
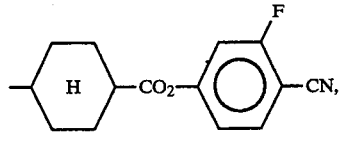
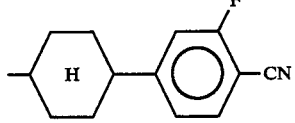
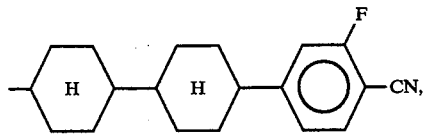
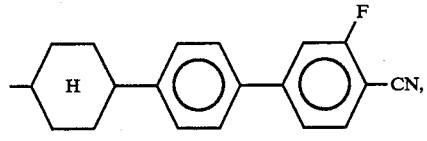
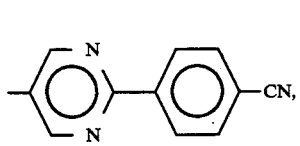

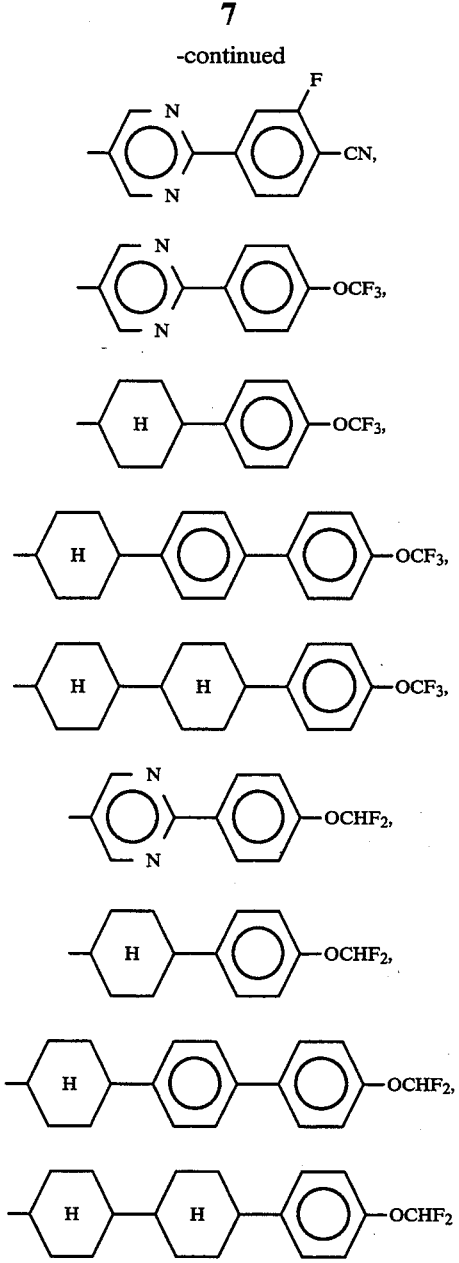

Particularly preferred compounds of the general formula (I) are also those in which $A^1$, $A^2$ and $A^3$ are identical or different, unsubstituted 1,4-phenylene, mono- or di-fluoro-substituted, 1,4-phenylene, 1,4-cyclohexylene, pyridine-2,5-diyl or pyrimidine-2,5-diyl.

The novel cyclopropylalkyl or -alkenyl compounds are chemically, photochemically and thermally stable and have good mixture compatibility. Compared with the corresponding n-alkyl homologs, these compounds frequently have a lower melting point; in mixtures such as LC mixtures frequently result in lower melting points; and, a lower value for the optical anisotropy Δn.

A further solution of the said object is a liquid-crystal mixture containing at least one liquid-crystalline compound and containing, as the liquid-crystalline compound, at least one compound of the general formula (I).

The liquid-crystal mixtures comprise 2 to 20, preferably 2 to 15, components, including at least one of the compounds according to the invention. The other components are preferably selected from known compounds having nematic, cholesteric and/or tilted smectic phases, including, for example, Schiff bases, biphenyls, terphenyls, phenylcyclohexanes, cyclohexylbiphenyls, pyrimidines, cinnamic acid esters, cholesterol esters and various bridged, polynuclear p-alkylbenzoic acid esters with terminal polar groups. In general, commercially available liquid-crystal mixtures exist, even before addition of the compound(s) according to the invention, as mixtures of a very wide variety of components of which at least one is mesogenic, i.e., exhibits a liquid crystal phase [=at least one enantiotropic (clear point>melting point) or monotropic (clear point<melting point) mesophase formation can be expected] as the compound, in derivatized form or mixed with certain cocomponents.

The liquid-crystal mixtures generally contain 0.01 to 70% by weight, in particular 0.05 to 50% by weight, of the compound(s) according to the invention.

The compounds according to the invention can be prepared by standard reactions known per se from mesogenic monofunctional reactive parent structures by linking with likewise monofunctional reactive cyclopropylalkyl compounds, where the synthesis of the two components may be regarded as known.

Thus, for example, mesogenic hydroxyl or mercapto compounds can be linked to cyclopropyl-alkanols in the presence of triphenylphosphine/azodicarboxylic acid diesters (Mitsunobu reaction, for example in J. Chem. Soc. Perkin Trans. 1975, 461). It is also possible to react the alkali metal salts or alkaline earth metal salts of these mesogenic hydroxyl or mercapto compounds, produced separately or intermediately, with halo-, toluenesulfonyloxy- or methylsulfonyloxy-cyclopropylalkyl compounds (Williamson reaction, for example in Patai, The Chemistry of the Ether Linkage, Interscience Publishers, N.Y. 1967, pp. 446–468).

However, it is also possible to react mesogenic carboxylic acids with cyclopropylalkanols under condensation conditions (for example in March, Advanced Organic Chemistry, 2nd Ed., McGraw-Hill, Kogakuska Ltd., Tokyo 1977, pp. 363–365. This is also possible in the same way using mesogenic hydroxyl or mercapto compounds and cyclopropyl-alkanoic acids.

The cyclopropylalkyl compounds necessary for the linkage are prepared by standard methods; in this respect, reference is made to the abovementioned publications (US-A) by Henrick et al.

In addition, cyclopropyl compounds can be prepared by the Simmons-Smith reaction (see, for example, in March, Advanced Organic Chemistry, pp. 793–794) from the corresponding olefins.

The following non-limiting Examples are given by way of illustration only and are not to be considered a limitation of this invention.

EXAMPLES

In the Examples below, parts by weight have the same relationship to parts by volume as the kilogram to the liter.

EXAMPLE 1

5-Heptyloxy-2-[4-(9-cyclopropyl-nonyl)oxy-phenyl]-pyrimidine

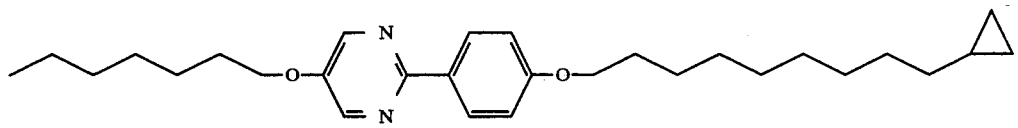

0.5 part by weight of 9-cyclopropylnonanol and 0.95 part by weight of 4-(5-heptyloxypyrimidine-2-yl)-phenol were added to a solution of 0.52 part by volume of diethyl azodicarboxylate and 0.85 part by weight of triphenylphosphine. After a reaction time of 24 hours, the solvent was removed by distillation and the residue was purified chromatographically ($SiO_2/CH_2Cl_2$). After recrystallization from 2-propanol, 0.52 part by weight of colorless crystals were obtained.

Phase sequence: C 56.4 $S_c$ 71.3 $S_A$ 83.4 N 85.1 I

The syntheses below were carried out in accordance with the procedure of Example 1, adjusting the quantities appropriately.

EXAMPLE 2

5-Hexyl-2-[4-(9-cyclopropyl-nonyl)oxy-phenyl]pyrimidine

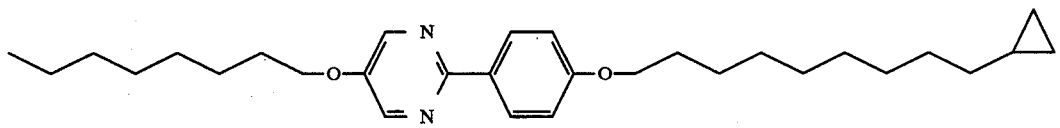

Phase sequence: C 44 N 53 I

EXAMPLE 3

5-Octyl-2-[4-(9-cyclopropyl-nonyl)oxy-phenyl]pyrimidine

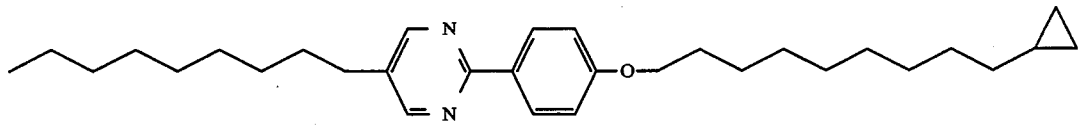

Phase sequence: C 41.3 $S_c$ 51 $S_A$ 57.6 N 60.2 I n∥ 1.616 n⊥ 1.486 Δn=0.13 (at 45° C., 589 nm)

Measurement method: An important characteristic quantity for the quality of the contrast of a LC display is the optical birefringence Δn=n∥ −n⊥. n∥ and n⊥ are the refractive indices for light polarized parallel or perpendicular to the director n. Both refractive indices can be determined as a function of temperature and wavelength using an Abbé refractometer.

EXAMPLE 4

5-Octyloxy-2-[4-(9-cyclopropyl-nonyl)oxy-phenyl]-pyrimidine

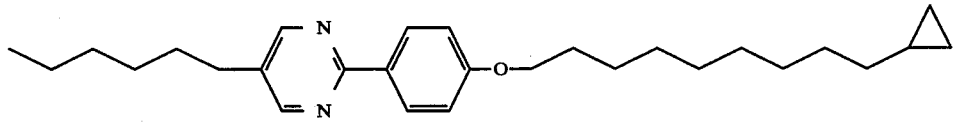

Phase sequence: C 69.2 $S_c$ 75.8 $S_A$ 90.2 I

EXAMPLE 5

5-Nonyl-2-[4-(9-cyclopropyl-nonyl)oxy-phenyl]pyrimidine

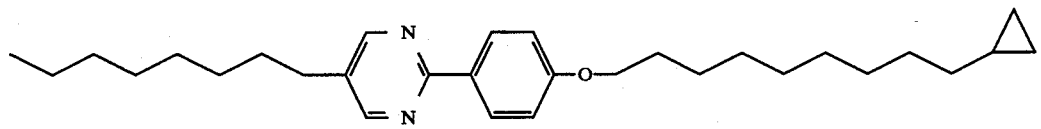

Phase sequence: C 52.8 $S_c$ 56.8 $S_A$ 67.2 I

EXAMPLE 6

5-Decyl-2-[4-(9-cyclopropyl-nonyl)oxy-phenyl]pyrimidine

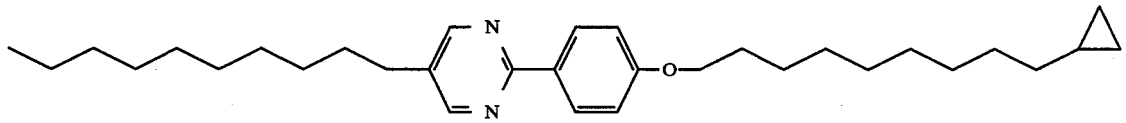

Phase sequence: C 44 $S_c$ 64.9 $S_A$ 67.7 I

EXAMPLE 7

5-Undecyl-2-[4-(9-cyclopropyl-nonyl)oxy-phenyl]-pyrimidine

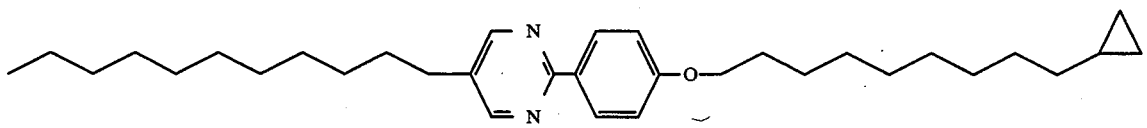

Phase sequence: C 48 $S_c$ 70.2 $S_A$ 71.8 I

EXAMPLE 8

5-Undecyloxy-2-[4-(9-cyclopropyl-nonyl)oxy-phenyl]-pyrimidine

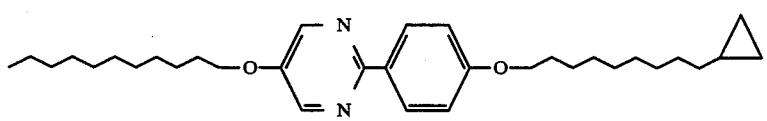

Phase sequence: C 68 $S_c$ 95 I

EXAMPLE 9

5-Dodecyl-2-[4-(9-cyclopropyl-nonyl)oxy-phenyl]-pyrimidine

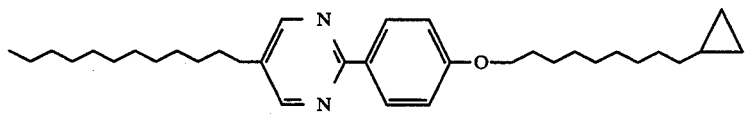

Phase sequence: C 52 $S_c$ 72.3 I

EXAMPLE 10

2-Decylthio-5-[4-(9-cyclopropyl-nonyl)oxy-phenyl]pyrimidine

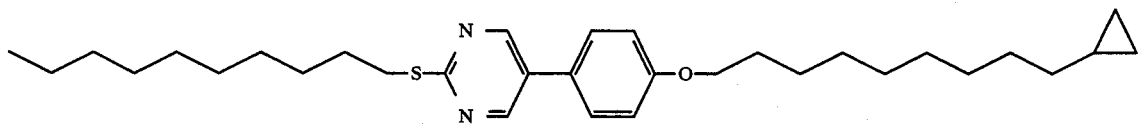

Phase sequence: C 67.5 [38 $S_2$ 57 $S_c$ 65] I

EXAMPLE 11

5-(9-Cyclopropyl-nonyl)oxy-2-(4-heptyloxy-phenyl)-pyrimidine

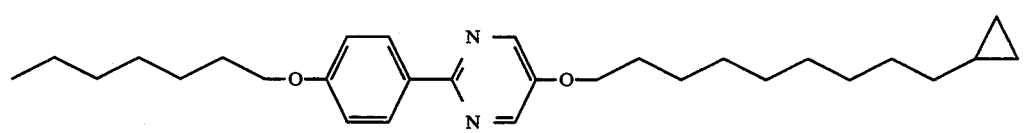

Phase sequence: C 64.7 $S_c$ 91 I

EXAMPLE 12

5-(9-Cyclopropyl-nonyl)oxy-2-(4-octyloxy-phenyl)-pyrimidine

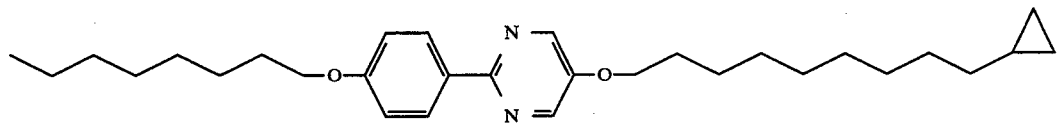

Phase sequence: C 63.7 $S_c$ 93.2 I

EXAMPLE 13

5-Octyl-2-[4-<5-((3S)-2,2-dimethylcyclopropyl)-3-methylpentyl>oxy-phenyl]pyrimidine

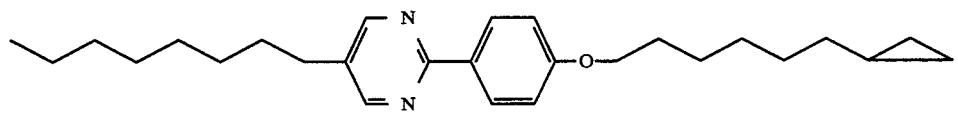

Phase sequence: C[−21.5 $S_A$ 16]18.5 I $[\alpha]^{25}_D$: −5.2 (c=5, CH$_2$Cl$_2$)

Measurement method: If a small amount of a chiral compound is added to a (non-chiral) solvent, the plane of linear-polarized light is rotated by the (characteristic) angle α; this angle is given as follows $[\alpha]^T_D$ (C=x, solv.), where the symbols have the following meaning:

x=concentration of the solution in g/l, solv.=solvent, D=589 nm (NaD line), T=temperature of the solution. The angle of rotation is determined in a polarimeter at a path length of 10 cm.

EXAMPLE 14

(2S,3S)-4-[5-(9-cyclopropyl-nonyl)oxy-pyrimidine-2-yl)-phenyl-2- chloro-3-methyl-pentanoate

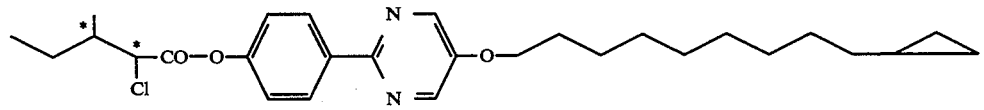

Phase sequence: C [38 $S_c$ 40 $S_A$ 44.3] 48.5 I
$[\alpha]^{25}_D$=−2.0 (c=4, CH$_2$Cl$_2$)

EXAMPLE 15

5-Octyl-2-[4-(6-cyclopropyl-hexyl)oxy-phenyl]pyrimidine

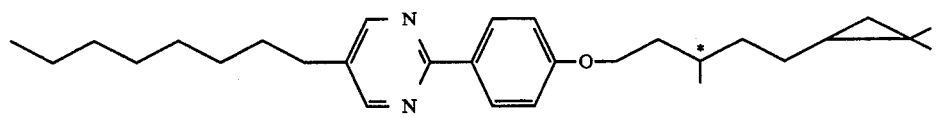

Phase sequence: C 39 $S_c$ 46 $S_A$ 50 N 59.5 I

EXAMPLE 16

5-Decyl-2-[4-(6-cyclopropyl-hexyl)oxy-phenyl]pyrimidine

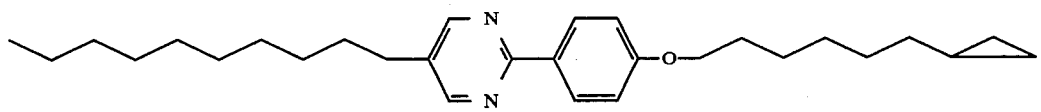

Phase sequence: C 42 $S_c$ 60 $S_A$ 65 I

EXAMPLE 17

5-Heptyloxy-2-[4-(6-cyclopropyl-hexyl)oxy-phenyl]-pyrimidine

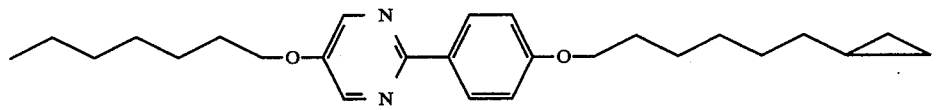

Phase sequence: C 54 $S_c$ 72 $S_A$ 78 N 88 I

EXAMPLE 18

5-Octyloxy-2-[4-(6-cyclopropyl-hexyl)oxy-phenyl]-pyrimidine

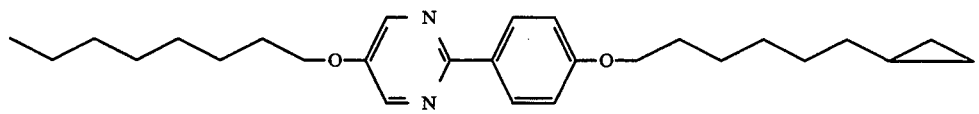

has an $S_c/S_A$ transition at 81, an $S_A/N$ transition at 89 and a clear point at 92° C.

EXAMPLE 19

5-(6-Cyclopropyl-hexyl)oxy-2-(4-nonyloxy-phenyl)-pyrimidine

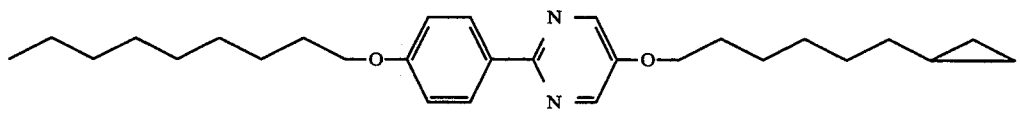

Phase sequence: C 56.5 $S_c$ 79 $S_A$ 85 N 89.5 I

EXAMPLE 20

5-(6-Cyclopropyl-hexyl)oxy-2-(4-undecyloxy-phenyl)-pyrimidine

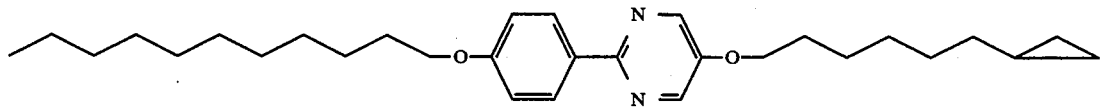

Phase sequence: C 57.5 $S_c$ 76.5 $S_A$ 86.7 N 87 I

EXAMPLE 21

5-(6-Cyclopropyl-hexyl)oxy-2-(4-dodecyloxy-phenyl)-pyrimidine

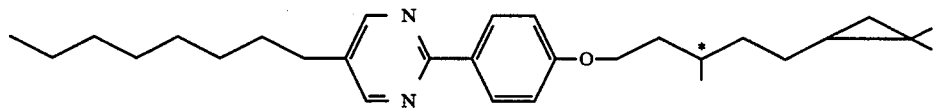

Phase sequence: C 61 $S_c$ 77 $S_A$ 87 I

EXAMPLE 22 trans-2-<9-[4-(5-octyl-pyrimidin-2-yl)phenyloxy]nonyl>-cyclopropaneethylcarboxylate

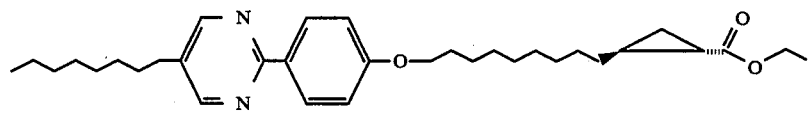

Phase sequence: C [11 $S_c$ 36 $S_A$] 38 I

EXAMPLE 23

5-Octyl-2-[4-(7-cyclopropyl-heptyl)oxy-phenyl]pyrimidine

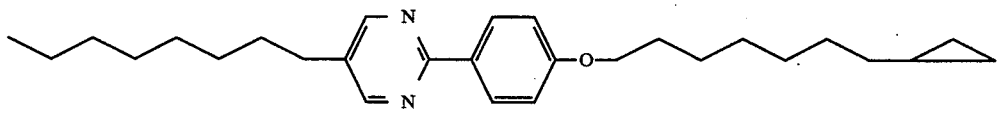

Phase sequence: C 33 $S_c$ 45.5 $S_A$ 54.6 N 58.4 I

EXAMPLE 24

5-(7-Cyclopropyl-heptyl)oxy-2-(4-nonyloxy-phenyl)-pyrimidine

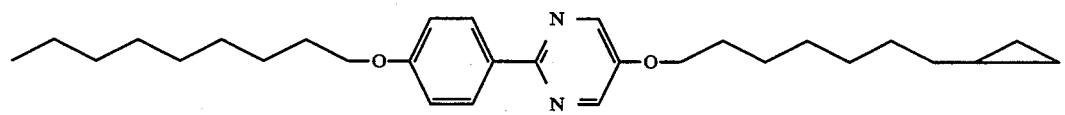

Phase sequence: C 60 $S_c$ 87.9 $S_A$ 90.4 I

EXAMPLE 25

5-(7-Cyclopropyl-heptyl)oxy-2-(4-undecyloxy-phenyl)-pyrimidine

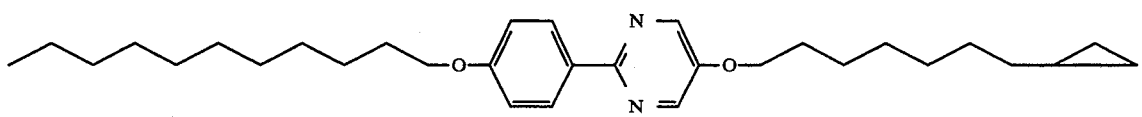

Phase sequence: C 53.4 S$_c$ 87.6 S$_A$ 90.5 I

EXAMPLE 26

5-(7-Cyclopropyl-heptyl)oxy-2-(4-dodecyloxy-phenyl)-pyrimidine

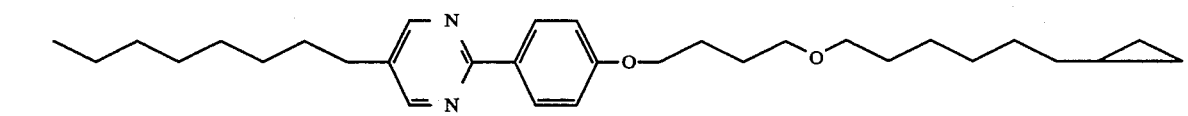

Phase sequence: C 67.4 S$_c$ 88.1 S$_A$ 90.5 I

EXAMPLE 27

5-Octyloxy-2-[4-(7-cyclopropyl-heptyl)oxy-phenyl]-pyrimidine

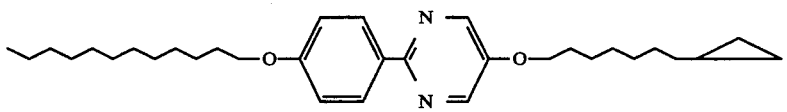

Phase sequence: C 60 S$_c$ 78.2 S$_A$ 90 N 90.2 I

EXAMPLE 28

2-Octylthio-5-[4-(7-cyclopropyl-heptyl)oxy-phenyl]-pyrimidine

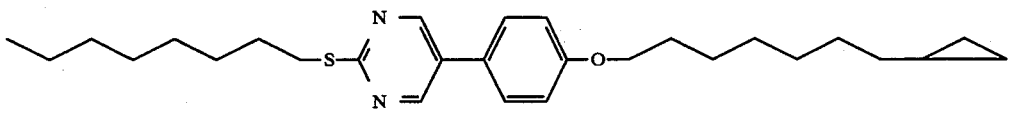

Phase sequence: C [41 S$_3$ 42 S$_c$ 55.5] 61.6 S$_A$ 62.2 I

EXAMPLE 29

5-Octyl-2-[4-(11-cyclopropyl-5-oxa-undecyl)oxy-phenyl]pyrimidine

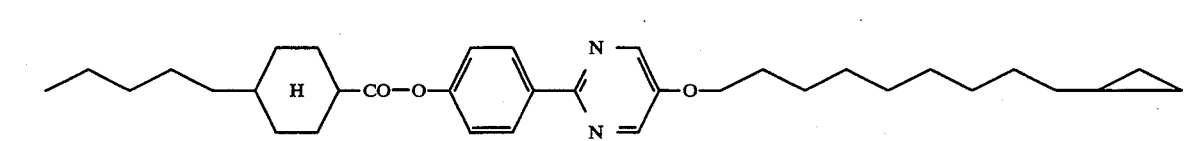

Phase sequence: C [16 S$_c$ 25.6 N 31] 40.9 I

EXAMPLE 30

5-(9-Cyclopropyl-nonyl)oxy-2-[4-(trans-4-pentyl-cyclohexyl)-carbonyloxy-phenyl]pyrimidine

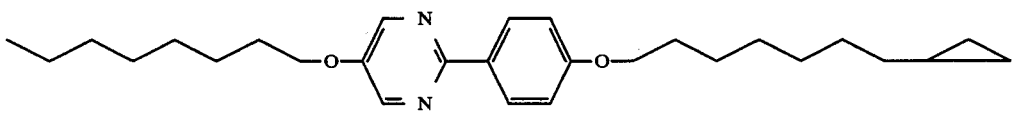

Phase sequence: C [76 S$_2$ 84.3] 86.5 S$_c$ 129.2 N 179 I

EXAMPLE 31

5-(6-Cyclopropyl-5-oxa-hexyl)oxy-2-(4-nonyloxy-phenyl)pyrimidine

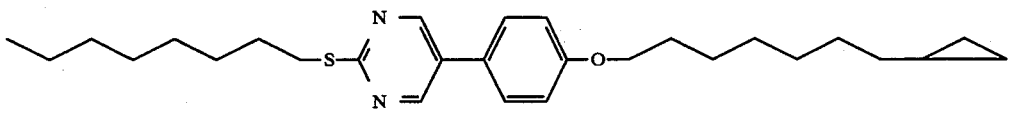

Phase sequence: C [58 S$_c$ 58.4 N 72] 72.4 I

EXAMPLE 32

5-Octyl-2-[4-(6-cyclopropyl-5-oxa-hexyl)oxy-phenyl]-pyrimidine

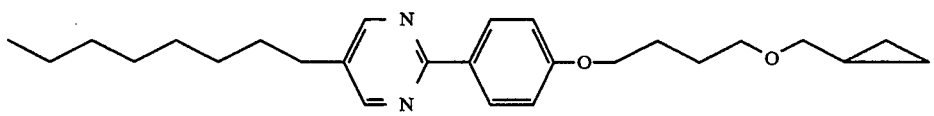

Phase sequence: C [-4 $S_c$ 22] 28.5 N 40.2 I

EXAMPLE 33

5-(9-Cyclopropyl-nonyl)oxy-2-(4-undecyloxy-phenyl)-pyrimidine

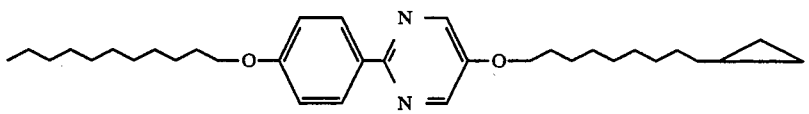

Phase sequence: C 55 $S_c$ 94.2 I

EXAMPLE 34

5-(9-Cyclopropyl-nonyl)oxy-2-(4-dodecyloxy-phenyl)-pyrimidine

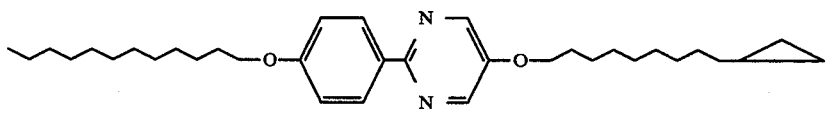

Phase sequence: C 63 $S_c$ 94.2 I

EXAMPLE 35

5-Decyl-2-[4-(7-cyclopropyl-heptyl)oxy-phenyl]-pyrimidine

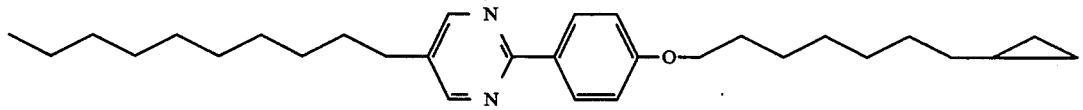

Phase sequence: C 40.3 $S_c$ 61 $S_A$ 66.2 I

EXAMPLE 36

5-(7-Cyclopropyl-heptyl)oxy-2-(4-octyloxy-phenyl)-pyrimidine

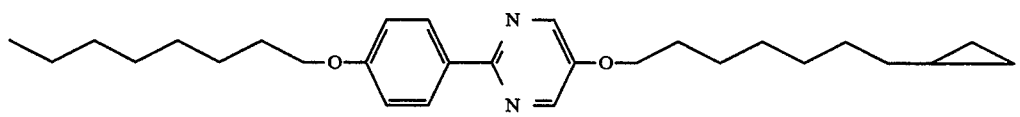

Phase sequence: C 56.5 $S_c$ 89.1 $S_A$ 91.6 I

EXAMPLE 37

5-Dodecyl-2-[4-(11-cyclopropyl-undecyl)oxy-phenyl]-pyrimidine

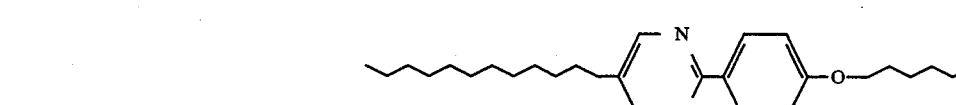

Phase sequence: C 72 $S_c$ 95.3 I

EXAMPLE 38

5-Decyl-2-[4-(11-cyclopropyl-undecyl)oxy-phenyl]-pyrimidine

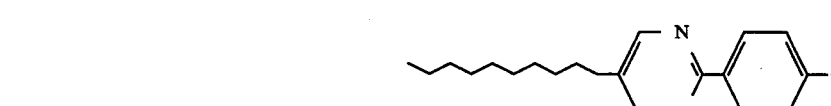

Phase sequence: C 51.7 $S_c$ 65.6 $S_A$ 67.3 I

EXAMPLE 39

5-(7-Cyclopropyl-heptyl)oxy-2-(4-hexyloxy-phenyl)pyrimidine

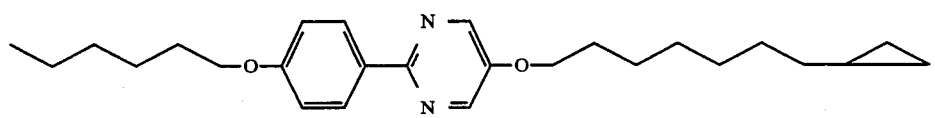

Phase sequence: C 51.8 S$_c$ 86.5 S$_A$ 89.6 N 89.8 I

EXAMPLE 40

5-Octyl-2-[4(8-cyclopropyl-octyl)oxy-phenyl]pyrimidine

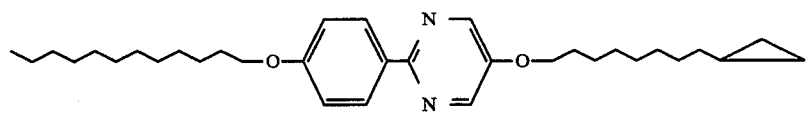

Phase sequence: C 35 S$_c$ 51.5 S$_A$ 55.5 N 61.2 I

EXAMPLE 41

5-(8-Cyclopropyl-octyl)oxy-2-(4-nonyloxyphenyl)-pyrimidine

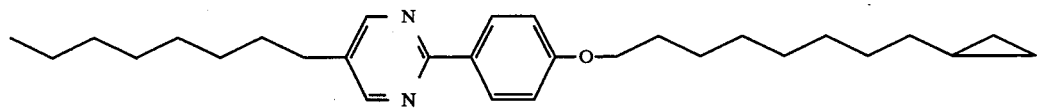

Phase sequence: C 56.2 S$_c$ 91.8 S$_A$ 93 I

EXAMPLE 42

5-(8-Cyclopropyl-octyl)oxy-2-(4-undecyloxy-phenyl)-pyrimidine

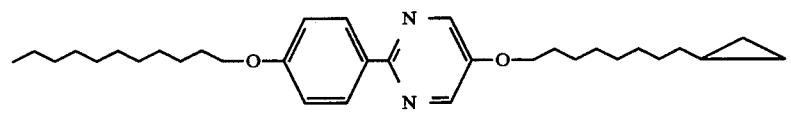

Phase sequence: C 53.6, S$_c$ 92.3 S$_A$ 93.1 I

EXAMPLE 43

5-(8-Cyclopropyl-octyl)oxy-2-(4-dodecyloxy-phenyl)-pyrimidine

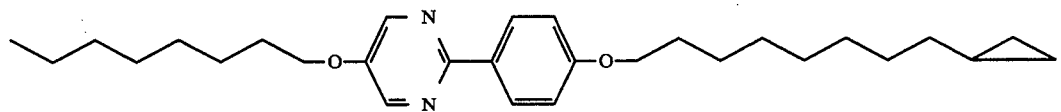

Phase sequence: C 54.9 S$_c$ 92.3 S$_A$ 93 I

EXAMPLE 44

5-Octyloxy-2-[4-(8-cyclopropyl-octyl)oxy-phenyl]-pyrimidine

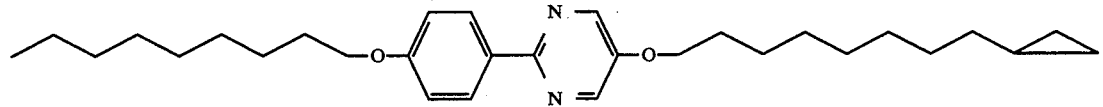

Phase sequence: C 51 S$_c$ 79.2 S$_A$ 91 N 91.6 I

EXAMPLE 45

2-Octylthio-5-[4-(8-cyclopropyl-octyl)oxy-phenyl]-pyrimidine

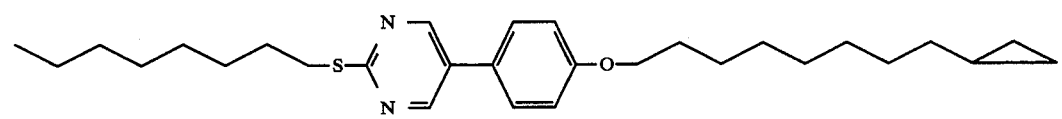

Phase sequence: C [42.2 S$_c$ 59.5 S$_A$ 62.5] 64.7 I

EXAMPLE 46

5-(8-Cyclopropyl-octyl)oxy-2-(4-hexyloxy-phenyl)-pyrimidine

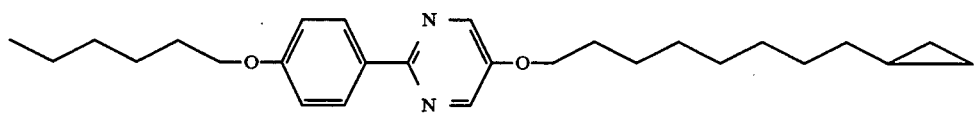

Phase sequence: C 54.1 $S_c$ 88.2 $S_A$ 90.8 I

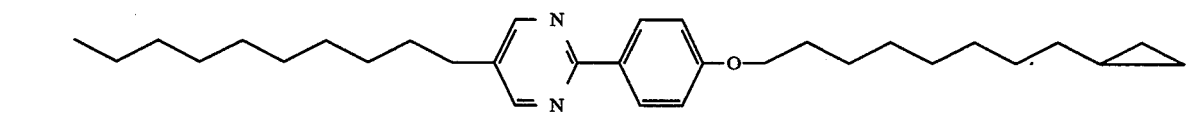

EXAMPLE 47

5-(8-Cyclopropyl-octyl)oxy-2-(4-oxtyloxy-phenyl)-pyrimidine

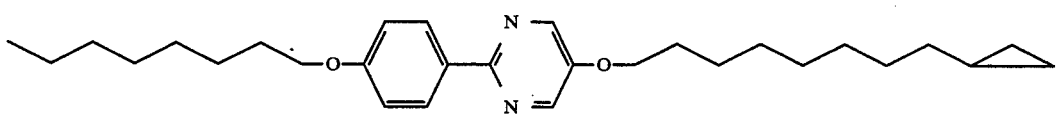

Phase sequence: C 56.4 $S_c$ 91.7 $S_A$ 92.9 I

EXAMPLE 48

5-(11-Cyclopropyl-undecyl)oxy-2-(4-dodecyloxy-phenyl)pyrimidine

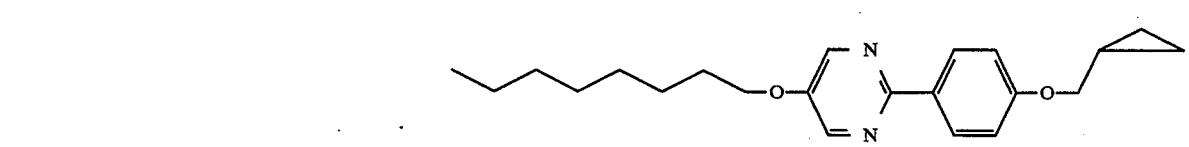

Phase sequence: 54.6 $S_c$ 73.8 I

EXAMPLE 49

3-(9-Cyclopropyl-nonyl)oxy-6-(4-octyloxy-phenyl)-pyridazine

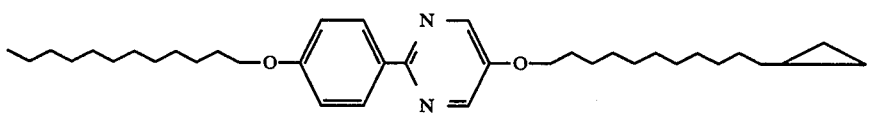

Phase sequence: C [82 $S_c$ 95.7] 100 I

EXAMPLE 50

5-Decyl-2-[4-(8-cyclopropyl-octyl)oxy-phenyl]pyrimidine

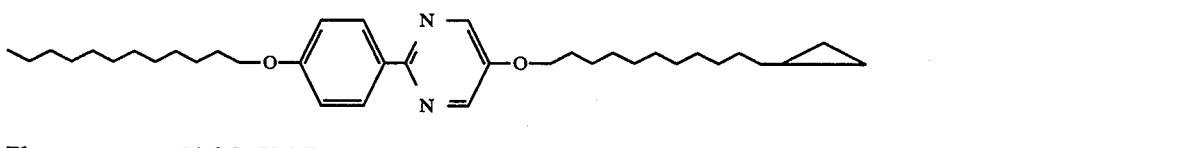

Phase sequence: C 42.3 $S_c$ 62.5 $S_A$ 67.2 I

EXAMPLE 51

5-Octyloxy-2-[4-(cyclopropylmethyl)oxy-phenyl]-pyrimidine

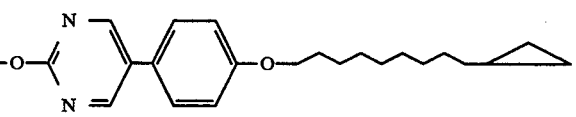

Phase sequence: C 59 $S_c$ 62.8 $S_A$ 72.9 N 73.6 I

EXAMPLE 52

2-(9-Cyclopropyl-nonyl)oxy-5-[4-(9-cyclopropyl-nonyl-oxy)phenyl]pyrimidine

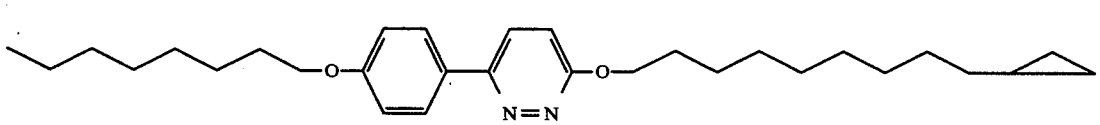

Phase sequence: C [79.3 $S_c$ 79.5] 89.4 I

EXAMPLE 53

2-(9-Cyclopropyl-nonyl)oxy-5-(4-decyloxyphenyl)-pyrimidine

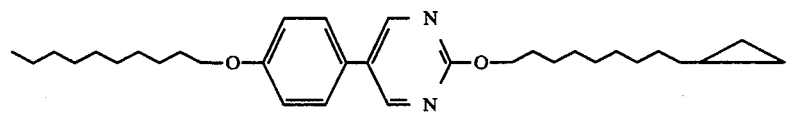

Phase sequence: C [70 S₃ 70.55 S_c 84 S_A 87.6] 88 I

EXAMPLE 54

4-(2-Octylthiopyrimidin-5-yl)phenyl trans-2-hexyl-cyclopropanecarboxylate

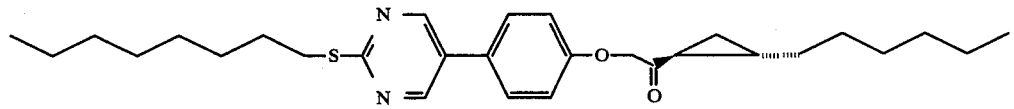

Phase sequence: C 40.5 I

EXAMPLE 55

5-(8-Cyclopropyl-octyl)oxy-2-(4-decyloxy-phenyl)-pyrimidine

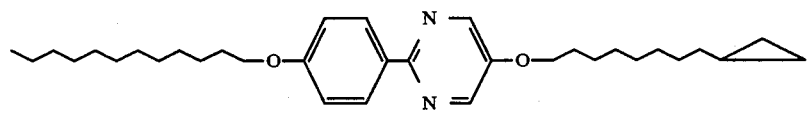

Phase sequence: C 58.5 S_c 91.6 S_A 92 I

EXAMPLE 56

5-(8-Cyclopropyl-octyl)oxy-2-[4-butyloxy-phenyl]pyrimidine

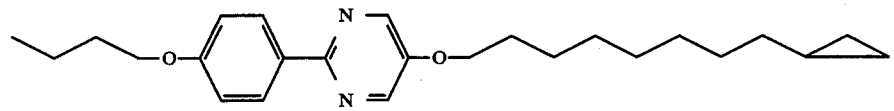

Phase sequence: C 55.4 S_c 81 S_A 87.8 I

EXAMPLE 57

(R)-4-[2-(9-Cyclopropyl-nonyl)oxy-pyrimidin-5-yl]-phenyl 2,2-dimethyl-1,3-dioxolane-4-carboxylate

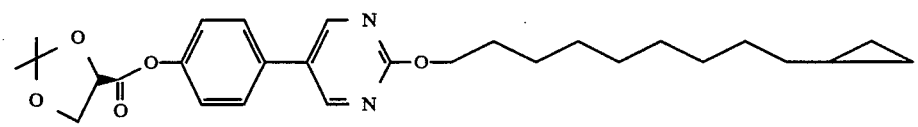

Phase sequence: C 84 I [α]²⁰_D: +5.46 (C=2, CH₂Cl₂)

EXAMPLE 58

(2S, 3S)-4-[2-(9-Cyclopropyl-nonyl)oxy-pyrimidin-5-yl]-phenyl 2-chloro-3-methyl-pentanoate

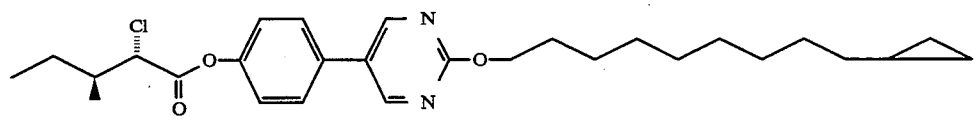

Phase sequence: C 81 I [α]²⁰_D: +1.2 (C=2, CH₂Cl₂)

EXAMPLE 59

5-Octyl-2-[4-(4-cyclopropyl-butyl)oxy-phenyl]pyrimidine

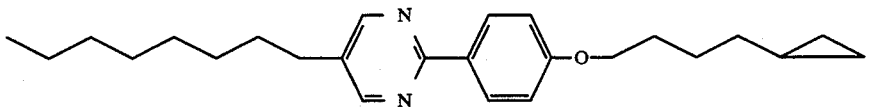

Phase sequence: C [16 S_c 37 S_A 43.6] 45 N 56 I

EXAMPLE 60

5-Decyl-2-[4-cyclopropyl-butyl)oxy-phenyl]pyrimidine

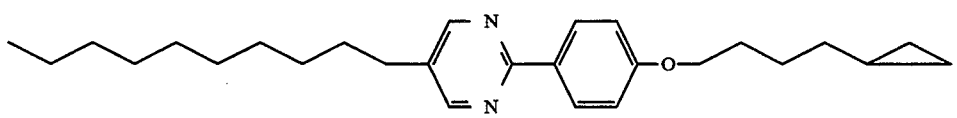

Phase sequence: C [47 $S_c$ 48] 64 N 88 I

EXAMPLE 61

5-(4-Cyclopropyl-butyl)oxy-2-(4-hexyloxy-phenyl)-pyrimidine

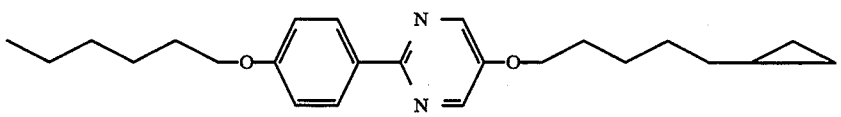

Phase sequence: C [47 $S_c$ 48] 64 N 88 I

EXAMPLE 62

5-Octyl-2-[4-(5-cyclopropyl-pentyl)oxy-phenyl]pyrimidine

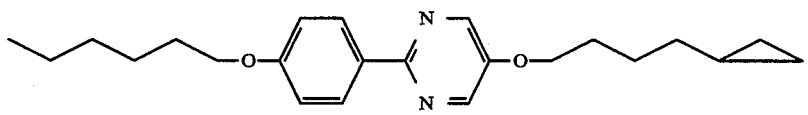

Phase sequence: C [18 $S_c$ 34] 38 $S_A$ 51 N 54 I

EXAMPLE 63

5-Decyl-2-[4-(5-cyclopropyl-pentyl)oxy-phenyl]-pyrimidine

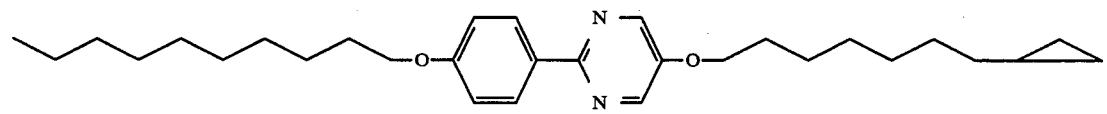

Phase sequence: C 48 $S_c$ 53 $S_A$ 62 I

EXAMPLE 64

5-(5-Cyclopropyl-pentyl)oxy-2-(4-hexyloxy-phenyl)-pyrimidine

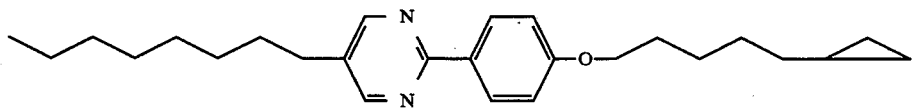

Phase sequence: C 53 $S_c$ 73 $S_A$ 75 N 86 I

EXAMPLE 65

5-(7-Cyclopropyl-heptyl)oxy-2-(4-decyloxy-phenyl)-pyrimidine

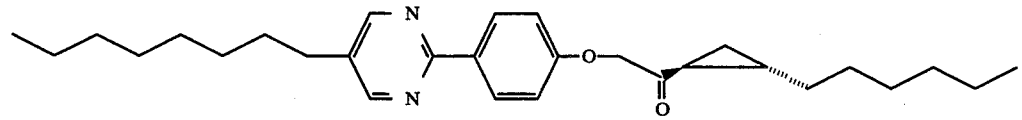

Phase sequence: C 55.7 $S_c$ 90 $S_A$ 92.5 I

EXAMPLE 66

4-(5-Octyl-pyrimidin-2-yl)phenyl trans-2-hexyl-cyclo-propylcarboxylate

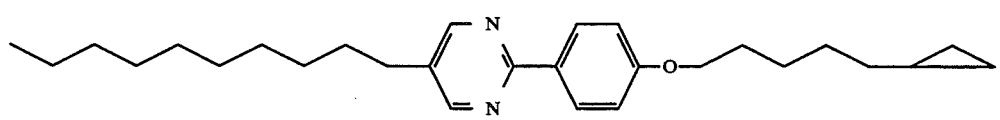

Phase sequence: C 44 I

EXAMPLE 67

4-[2-(9-cyclopropylnonyl)oxy-pyrimidin-5-yl]phenyl (2R,3R)-3-propyl-oxirane-2-carboxylate

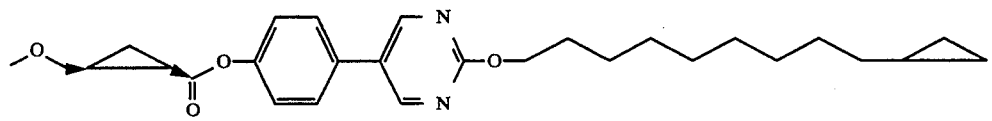

Phase sequence: C 75 I [α]$^{20}_D$: −9.6 (C=2, CH$_2$Cl$_2$)

EXAMPLE 68

4-[2-(9-Cyclopropylnonyloxy)-pyrimidin-5-yl]phenyl (2S)-2-fluoro-3-methyl-butanoate

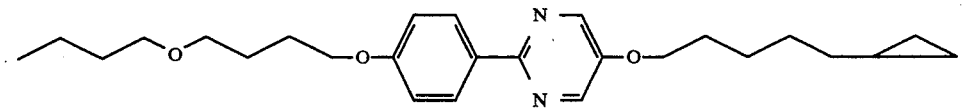

Phase sequence: X [63 S$_A$ 64] 78 I [α]$^{20}_D$: −1.0 (C=2, CH$_2$Cl$_2$)

EXAMPLE 69

2-(4-Hexyloxy-phenyl)-5-[4-(6-cyclopropyl-hexyloxy)-phenyl]pyrimidine

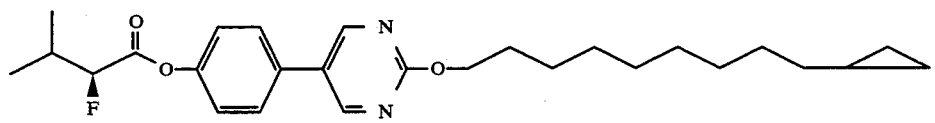

Phase sequence: X [77 S$_4$ 103]110 S$_3$ 129 S$_c$ 189 S$_A$ 198 I

EXAMPLE 70

5-(4-Cyclopropyl-butyloxy)-2-[4-(5-oxa-nonyloxy)-phenyl]pyrimidine

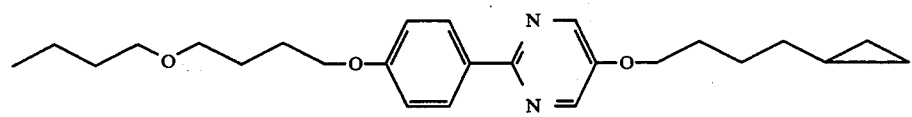

Phase sequence: C 42 S$_c$ 45 S$_A$ 47 N 64 I

EXAMPLE 71

5-(5-Cyclopropyl-pentyloxy)-2-[4-(5-oxa-nonyloxy)-phenyl]pyrimidine

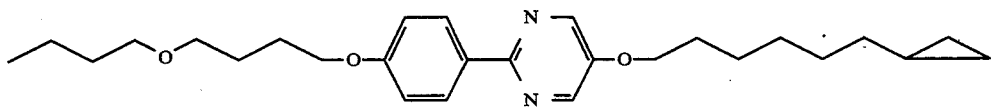

Phase sequence: X 39 S$_c$ 63 S$_A$ 65 N 67 I

EXAMPLE 72

5-(6-Cyclopropyl-hexyloxy)-2-[4-(5-oxa-nonyloxy)-phenyl]pyrimidine

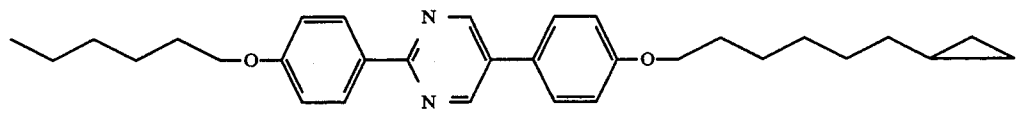

Phase sequence: X 46 S$_c$ 66 S$_A$ 67 N 69 I

EXAMPLE 73

5-(7-Cyclopropyl-heptyloxy)-2-[4-(5-oxa-nonyloxy)-phenyl]pyrimidine

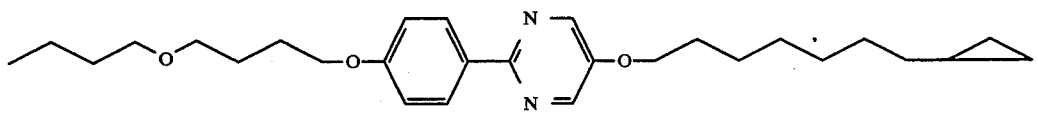

Phase sequence: C 43 S$_c$ 73 I

EXAMPLE 74

5-Cyclopropylmethyloxy-2-(4-octyloxyphenyl)pyrimidine

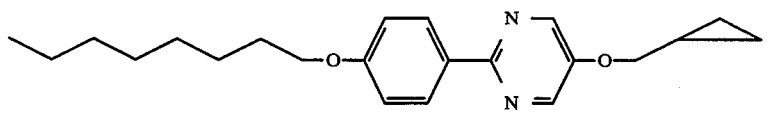

Phase sequence: C 63 N 64 I

EXAMPLE 75

5-Octyl-2-[4-(6-cyclopropyl-hexyloxy)phenyl]pyrimidine

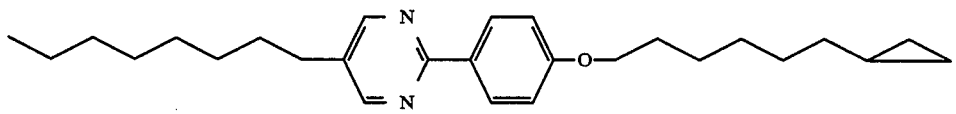

Phase sequence: C 37 $S_c$ 46 $S_A$ 50 N 59 I

EXAMPLE 76

5-Octyloxy-2-[4-(6-cyclopropyl-hexyloxy)phenyl]pyrimidine

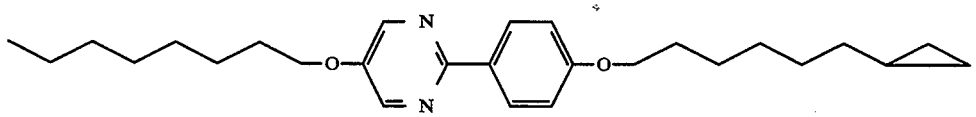

Phase sequence: C 56 $S_c$ 80 $S_A$ 88 N 91 I

EXAMPLE 77

5-(6-Cyclopropyl-hexyloxy)-2-(4-octyloxyphenyl)-pyrimidine

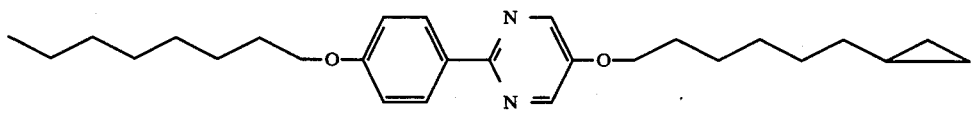

Phase sequence: C 56 $S_c$ 78 $S_A$ 84 N 89 I

EXAMPLE 78

2-[4-(7-Cyclopropyl-heptyloxy)phenyl]-5-octyl-pyridine

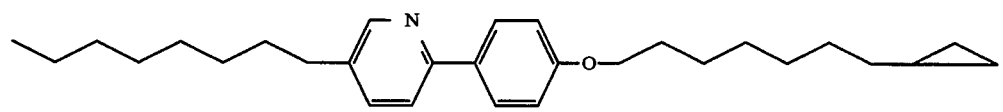

Phase sequence: C 49 $S_2$ 63 $S_c$ 72 I

EXAMPLE 79

2-[4-(11-Cyclopropyl-undecyloxy)phenyl]-5-octyl-pyridine

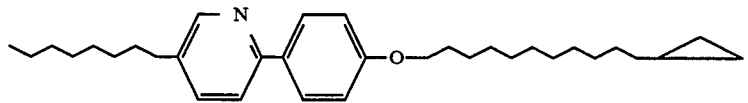

Phase sequence: C 57 $S_2$ 63 $S_c$ 72 I

EXAMPLE 80

2-(trans-4-Pentyl-cyclohexyl)-5-[4-(11-cyclopropyl-undecyloxy)phenyl]-1,3,4-thiadiazole

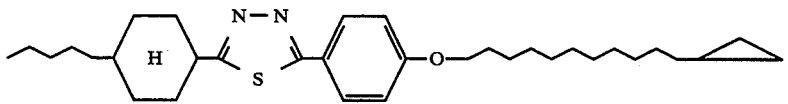

Phase sequence: C 111 $S_c$ 113 $S_A$ 156 N 157 I

EXAMPLE 81

4-(5-Octyl-pyrimidin-2-yl)phenyl 7-cyclopropyl-heptanoate

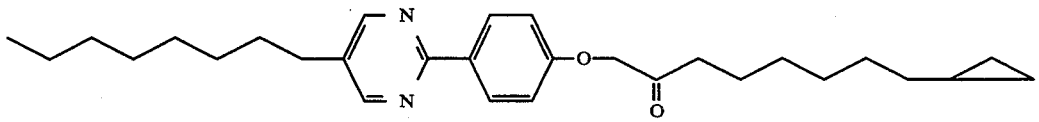

Phase sequence: C [36 $S_c$ 40.5 $S_A$ 44 N 46] 51 I

EXAMPLE 82

4-(5-Decyl-pyrimidin-2-yl)phenyl 7-cyclopropyl-heptanoate

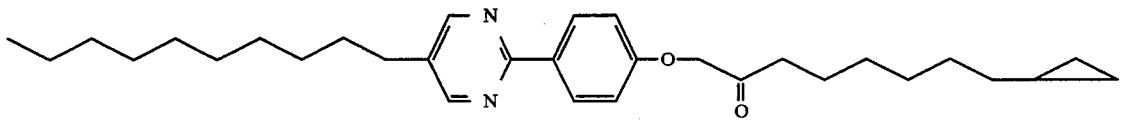

Phase sequence: C 48 $S_c$ 57 I

EXAMPLE 83

4-(5-Octyloxy-pyrimidin-2-yl)phenyl 7-cyclopropyl-heptanoate

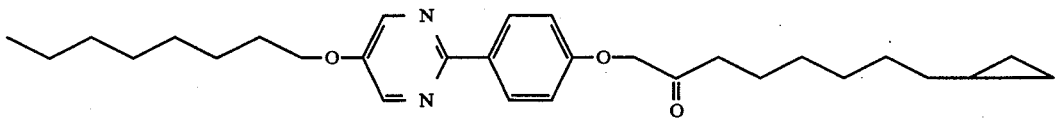

Phase sequence: C 62 $S_c$ 77 $S_A$ 84 N 84.3 I

EXAMPLE 84

A mixture comprising 55 mol-% of the compound of Example 6 and 45 mol-% of the compound of Example 3 exhibited the phase sequence C 31 $S_c$ 58 $S_A$ 64 I.

EXAMPLE 85

A mixture comprising 67 mol-% of the compound of Example 6 and 33 mol-% of the compound of Example 11 exhibited the phase sequence C 35 $S_c$ 74 $S_A$ 78 I.

EXAMPLE 86

A mixture comprising 20 mol-% of the compound of Example 6, 25.15 mol-% of (the mixture components, each of which is known) 5-octyloxy-2-(4-decyloxy-phenyl)-pyrimidine, 11 mol-% of 4-octyloxy-2-(4-octyloxy-phenyl)pyrimidine, 20 mol-% of 5-octyloxy-2-(4-hexyloxy-phenyl)pyrimidine and 23.85 mol-% of 5-octyloxy-2-(4-butyloxy-phenyl)pyrimidine exhibited the phase sequence C 11.5 $S_c$ 72 $S_A$ 88 N 90 I.

EXAMPLE 87

A mixture comprising 60 mol-% of the compound of Example 56 and 40 mol-% of the compound of Example 55 exhibited the phase sequence C 34 $S_c$ 82 $S_A$ 90 I.

EXAMPLE 88

A mixture comprising 62 mol-% of the compound of Example 43 and 38 mol-% of the compound of Example 37 exhibited the phase sequence C 48 $S_c$ 93 I.

EXAMPLE 89

A mixture comprising 57 mol-% of the compound of Example 43 and 43 mol-% of the compound of Example 65 exhibited the phase sequence C 36 $S_c$ 90 $S_A$ 92 I.

EXAMPLE 90

A mixture comprising 60 mol-% of the compound of Example 27 and 40 mol-% of the compound of Example 47 exhibited the phase sequence C 33 $S_c$ 85 $S_A$ 91 I.

EXAMPLE 91

A mixture comprising 45 mol-% of the compound of Example 24 and 55 mol-% of the compound of Example 71 exhibited the phase sequence C 25 $S_c$ 70 $S_A$ 77 N 79 I.

EXAMPLE 92

A mixture comprising 30 mol-% of the compound of Example 65 and 70 mol-% of the compound of Example 71 exhibited the phase sequence C 25 $S_c$ 70 $S_A$ 73 N 75 I.

EXAMPLE 93

A mixture comprising 40 mol-% of the compound of Example 76 and 60 mol-% of the compound of Example 56 exhibited the phase sequence C 35 $S_c$ 81 $S_A$ 90 I.

EXAMPLE 94

A mixture comprising 65 mol-% of the compound of Example 71 and 35 mol-% of the compound of Example 56 exhibited the phase sequence C 17 $S_c$ 69 $S_A$ 73 N 74 I.

Compared with a comparison mixture (binary mixture containing compounds of comparable chain lengths without a cyclopropyl radical) comprising 40 mol-% of 5-octyloxy-2-(4- octyloxy-phenyl)pyrimidine and 60 mol-% of 5-octyloxy-2-(4- hexyloxy-phenyl)pyrimidine which had the phase sequence C 39 $S_c$ 90 $S_A$ 98 N 100 I, Examples 93 and 94 had both a lower melting point and a greater melting point depression.

EXAMPLE 95

A mixture comprising 50 mol-% of 5-dodecyloxy-2-(4octyloxyphenyl)pyrimidine and 50 mol-% of the compound of Example 24 had the phase sequence C 33 $S_c$ 96 I. Compared with the comparison mixtures (binary mixtures of comparable chain lengths without a cyclopropyl radical) comprising 39 mol-% of 5-decyloxy-2-(4-octyloxy-phenyl)pyrimidine and 61 mol-% of 5-octyloxy-2-(4-decyloxyphenyl)pyrimidine which had the phase sequence C 39 $S_c$ 94 $S_A$ 100 I or comprising 60 mol-% of 5-octyloxy-2-(4-decyloxyphenyl)pyrimidine and 40 mol-% of 5-octyloxy-2-(4-dodecyloxyphenyl)-pyrimidine which had the phase sequence C 40 $S_c$ 86 $S_A$ 97 I, the mixture according to the invention has both a lower melting point and a greater melting point depression.

EXAMPLE 96

A mixture comprising:

30 mol-% of 5-octyloxy-2-(4-ethyloxy-phenyl)-pyrimidine 6 mol-% of 5-dodecyloxy-2-(4-butyloxy-phenyl)pyrimidine 15 mol-% of the compound of Example 24 19 mol-% of the compound of Example 71 20 mol-% of the compound of Example 56 10 mol-% of the compound of Example 43 had the phase sequence C 8 $S_c$ 68 $S_A$ 85 N 87.

EXAMPLE 97

A ferroelectric multicomponent mixture containing 10 mol-% of the compound of Example 62 in (R)Felix 001*) had the phase sequence C −5 $S_c$ 72 $S_A$*78 N* 93 I.

*) (C. Escher, H. R. Dübal, W. Hemmerling, I. Müller, D. Ohlendorf and R. Wingen, presented at "1st International Symposium on Ferroelectric Liquid Crystals, Arcachon, BOrdeaux-France, Sep. 21–23, 1987", commercially available mixture from Hoechst Aktiengesellschaft having the phase sequence C-7 $S_c$*79 $S_A$* 83 N* 99 I)

The mixture can readily be oriented by conventional methods and is bistable. At 25° C., the mixture exhibited a spontaneous polarization of −5.8 nC/cm² and had the following switching times:

τ0–90=212 μs
τ10–90=90 μs

The viscosity of the mixture was 65 mPas and the double effective tilt angle was 18°.

EXAMPLE 98

A ferroelectric mixture comprising:

85.5 mol-% of the mixture from Example 96, 9.5 mol-% of 4-(5-decyl-pyrimidin-2-yl)phenyl trans-4-pentyl-cyclohexanecarboxylate and 5 mol-% of 4-[2-((S)-7-methyl-nonyloxy)pyrimidin-5-yl]-phenyl (2S, 3S)-2-chloro-3-methyl-pentanoate had the phase sequence C 5 $S_c$* 72 $S_A$* 83 N* 88 I.

The mixture can readily be oriented by conventional methods and is bistable. At 25° C., the mixture exhibited a spontaneous polarization of −8.2 nC/cm² and had the following switching times:

τ0–90=139 μs
τ10–90=66 μs

The viscosity of the mixture was 280 mPas and the double effective tilt angle was 17°.

EXAMPLE 99

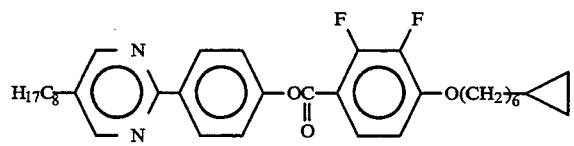

4-(5-octylpyrimidin-2-yl)phenyl 4-(6-cyclopropyl-hexyloxy)-2,3-difluorobenzoate

Preparation of 4-(6-cyclopropylhexyloxy)-2,3-difluoro-benzoic acid:

3.9 g of NaH (60% in oil) and 20 g of 6-cyclopropyl-hexanol were added to a solution of 8.5 g of difluorophenol in 100 ml of DMF. After a reaction time of 24 hours at room temperature, the solution was poured onto ice and extracted with $CH_2Cl_2$. After drying ($Na_2SO_4$) and removal of the solvent by distillation, 16.5 g of 6-cyclopropylhexyloxy-2,3-difluorobenzene were obtained as a colorless oil.

30 ml of butyllithium (1.6M in hexane) were added dropwise at −60° C. to a solution of 11.7 g of 6-cyclopropylhexyloxy-2,3-difluorobenzene in 70 ml of THF. After 5 hours at −60° C., $CO_2$ was passed in until saturation was complete. The solution was warmed to RT, the solvent was removed by distillation, 400 ml of $H_2O$ were added, and the mixture was acidified to pH 3 using acetic acid. The precipitate was filtered off with suction. 12.3 g of 4-(6-cyclopropylhexyloxy)-2,3-difluorobenzoic acid were obtained. Melting point 100°–108° C.

The following were obtained analogously:
4-(4-cyclopropylbutyloxy)-2,3-difluorobenzoic acid
4-(8-cyclopropyloctyloxy)-2,3-difluorobenzoic acid 1.2 g of 4-(6-cyclopropylhexyloxy)-2,3-difluorobenzoic acid were added to a solution of 0.84 g of dicyclohexyl-carbodiimide, 50 mg of dimethylaminopyridine and 1.15 g of 4-(5-octylpyrimidin-2-yl)phenol in 50 ml of methylene chloride. After a reaction time of 24 hours, the precipitate (dicyclohexylurea) was filtered off with suction. The filtrate was freed from solvent and chromatographed ($SiO_2$, $CH_2Cl_2$).

Recrystallization from hexane gave 1.1 g of 4-(5-octyl-pyrimidin-2-yl)phenyl 4-(6-cyclopropylhexyloxy)-2,3-difluorobenzoate.

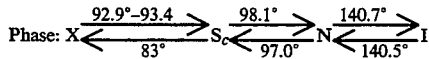

The following were obtained analogously:

EXAMPLE 100

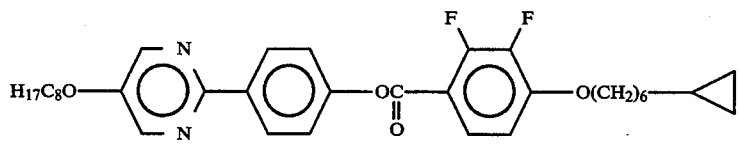

4-(5-octyloxypyrimidin-2-yl)phenyl
4-(6-cyclopropylhexyloxy)-2,3-difluorobenzoate Phases: X ⇌ 92.7° / 83° ⇌ S_C ⇌ 120.9°–121.6° / 121.4°–120.7° ⇌ N ⇌ 167.2° / 167.0° ⇌ I

EXAMPLE 101

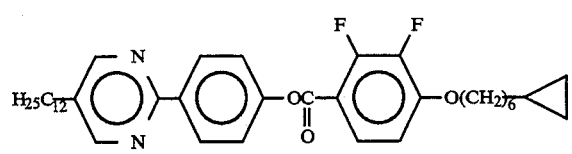

4-(5-dodecylpyrimidin-2-yl)phenyl
4-(6-cyclopropyl-hexyloxy)-2,3-difluorobenzoate Phases: X ⇌ 95.5°–95.9° / 89° ⇌ S_C ⇌ 114.0° / 113.8° ⇌ N ⇌ 133.8° / 133.6° ⇌ I

EXAMPLE 102

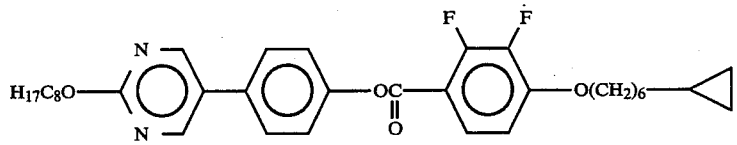

4-(2-octyloxypyrimidin-5-yl)phenyl
4-(6-cyclopropyl-hexyloxy)-2,3-difluorobenzoate Phases: X ⇌ 85.2° / 60° ⇌ S_C ⇌ 140.3° / 140.1° ⇌ S_1 ⇌ 168.8° / 168.6°–168.3° ⇌ I

EXAMPLE 103

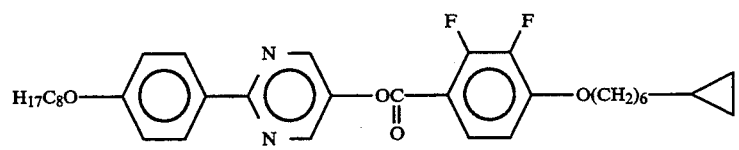

2-(4-octyloxyphenyl)pyrimidin-5-yl
4-(6-cyclopropyl-hexyloxy)-2,3-difluorobenzoate Phases: X ⇌ 89.5° / 88° ⇌ S_C ⇌ 155.4° / 155.3° ⇌ N ⇌ 178.4° / 178.2° ⇌ I

EXAMPLE 104

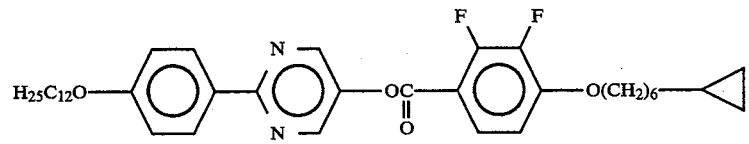

2-(4-dodecyloxyphenyl)pyrimidin-5-yl
4-(6-cyclopropyl-hexyloxy)-2,3-difluorobenzoate Phases: X ⇌ 89.3°–92.0° / 80° ⇌ S_C ⇌ 157.1° / 156.9° ⇌ N ⇌ 170° / 169.8° ⇌ I

EXAMPLE 105

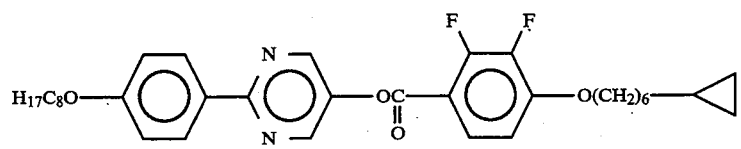

2-(4-octyloxyphenyl)pyrimidin-5-yl
4-(6-cyclopropyl-hexyloxy)-2,3-difluorobenzoate Phases: X ⇌ 79° / 70° ⇌ S_C ⇌ 164.5°–164.9° / 164.7°–164.2° ⇌ N ⇌ 184° / 183.8° ⇌ I

EXAMPLE 106

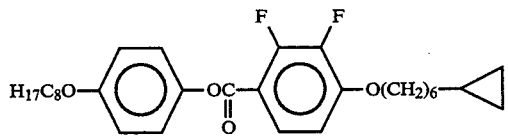

(4-octyloxy)phenyl
4-(6-cyclopropylhexyloxy)-2,3-difluorobenzoate

Phases: X $\underset{30°}{\overset{47.7°}{\rightleftarrows}}$ S$_c$ $\underset{59.0°}{\overset{59.2°}{\rightleftarrows}}$ N $\underset{72.1°}{\overset{72.3°}{\rightleftarrows}}$ I Comparison example

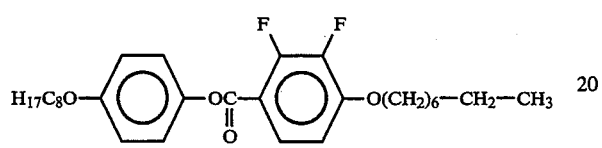

(4-octyloxy)phenyl 4-octyloxy-2,3-difluorobenzoate

Phases: X $\underset{21°}{\overset{48.8°}{\rightleftarrows}}$ S$_c$ $\underset{70.6°}{\overset{70.8°}{\rightleftarrows}}$ N $\underset{81.9°}{\overset{82.1°}{\rightleftarrows}}$ I Comparison of the substance from Example 106 according to the invention with the compound mentioned shows that the compound according to the invention had a lower melting point.

Replacement of the ethyl group by a cyclopropyl group reduced the melting point by about 1 degree.

EXAMPLE 107

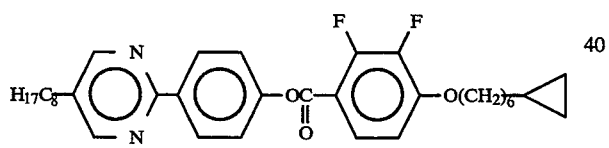

4-(5-octylpyrimidin-2-yl)phenyl
4-(6-cyclopropyl-hexyloxy)-2,3-difluorobenzoate

Phases: X $\underset{85.4°}{\overset{85.8°-87°}{\rightleftarrows}}$ S$_c$ $\underset{102.2°}{\overset{102.7°}{\rightleftarrows}}$ N $\underset{133.7°-133.5°}{\overset{133.8°}{\rightleftarrows}}$ I

EXAMPLE 108

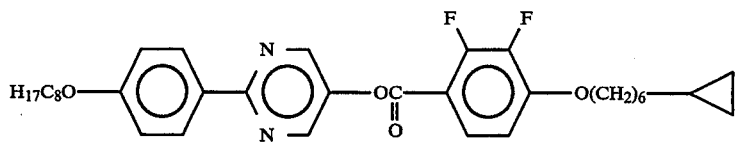

4-(5-octyloxypyrimidin-2-yl)phenyl
4-(6-cyclopropyl-hexyloxy)-2,3-difluorobenzoate Phases: X $\underset{74.4°}{\overset{84.1°-86.4°}{\rightleftarrows}}$ S$_c$ $\underset{125.2°}{\overset{125.5°}{\rightleftarrows}}$ N $\underset{160.2°}{\overset{160.6°}{\rightleftarrows}}$ I

EXAMPLE 109

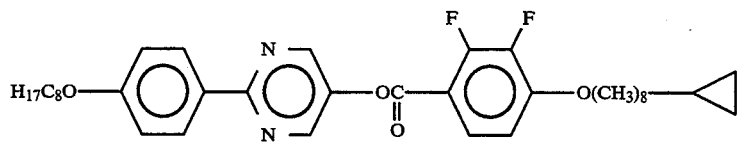

4-(5-octyloxyphenyl)pyrimidin-5-yl
4-(8-cyclopropyl-octyloxy)-2,3-difluorobenzoate Phases: X $\underset{86.5°}{\overset{96.8°}{\rightleftarrows}}$ S$_c$ $\underset{161.5°}{\overset{161.5°}{\rightleftarrows}}$ N $\underset{172.9°}{\overset{173.6°}{\rightleftarrows}}$ I

EXAMPLE 110

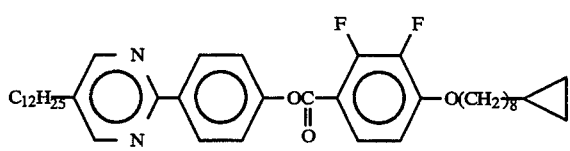

4-(5-dodecylpyrimidin-2-yl)phenyl
4-(8-cyclopropyl-octyloxy)-2,3-difluorobenzoate Phases: X $\underset{82.3°}{\overset{84.2°-86°}{\rightleftarrows}}$ S$_c$ $\underset{119°}{\overset{119.3°}{\rightleftarrows}}$ N $\underset{129.9°}{\overset{129.4°-130.1°}{\rightleftarrows}}$ I

EXAMPLE 111

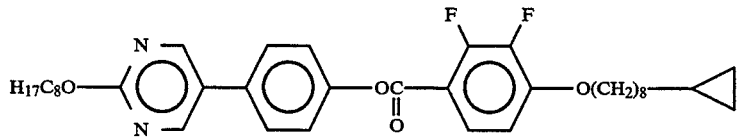

4-(2-octyloxypyrimidin-5-yl)phenyl
4-(8-cyclopropyl-octyloxy)-2,3-difluorobenzoate Phases: X $\underset{75°}{\overset{83.9°}{\rightleftarrows}}$ S$_c$ $\underset{146.2°}{\overset{146.4°}{\rightleftarrows}}$ N $\underset{164°}{\overset{164.2°}{\rightleftarrows}}$ I

EXAMPLE 112

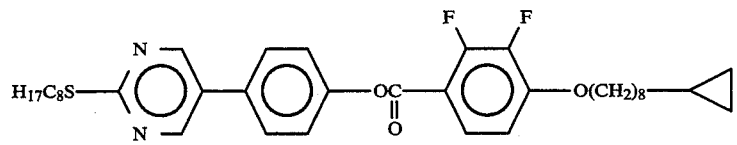

4-(2-octylthiopyrimidin-5-yl)phenyl 4-(8-cyclopropyl-octyloxy)-2,3-difluorobenzoate Phases: $X \underset{50°}{\overset{76.9°}{\rightleftarrows}} S_c \underset{131.5°}{\overset{131.7°}{\rightleftarrows}} N \underset{146.3°}{\overset{146.5°}{\rightleftarrows}} I$

EXAMPLE 113

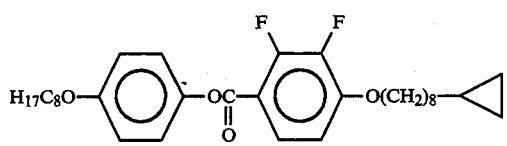

(4-octyloxy)phenyl 4-(8-cyclopropyloctyloxy)-2,3-difluorobenzoate

Phases: $X \underset{29°}{\overset{43.9°}{\rightleftarrows}} S_c \underset{67.5°}{\overset{67.7°}{\rightleftarrows}} N \underset{72.7°}{\overset{73°}{\rightleftarrows}} I$ Comparison Example

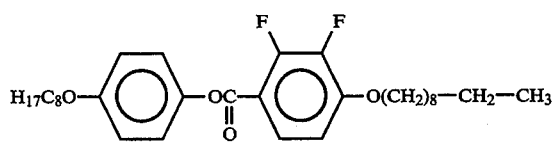

(4-decyloxy)phenyl 4-octyloxy-2,3-difluorobenzoate

Phases: $X \underset{34°}{\overset{48.4°}{\rightleftarrows}} S_c \underset{77.6°}{\overset{77.9°}{\rightleftarrows}} N \underset{81.6°}{\overset{81.8°}{\rightleftarrows}} I$ The compound from Example 113 according to the invention had a melting point which was lower by about 5 degrees than that of the comparison compound. Replacement of an ethyl group by a cyclopropyl group resulted in this lowering of the melting point which is favorable for practical applications.

EXAMPLE 114

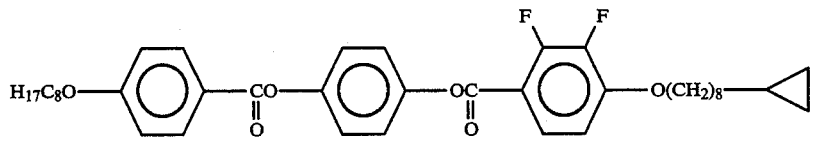

4-(4-octyloxybenzoyloxy)phenyl 4-(8-cyclopropyloctyloxy)-2,3-difluorobenzoate

Phases: $X \underset{80°}{\overset{92.3°}{\rightleftarrows}} S_c \underset{137.9°}{\overset{138.1°}{\rightleftarrows}} N \underset{172.2°}{\overset{172.4°}{\rightleftarrows}} I$

EXAMPLE 115

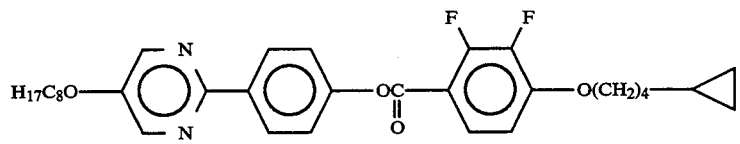

4-(5-octyloxypyrimidin-2-yl)phenyl 4-(4-cyclopropyl-butyloxy)-2,3-difluorobenzoate Phases: $X \overset{90.2°}{\longrightarrow} N \underset{142.2°}{\overset{145.5°}{\rightleftarrows}} I$, $83.1° \searrow \nearrow 83.1°$ $S_c$

EXAMPLE 116

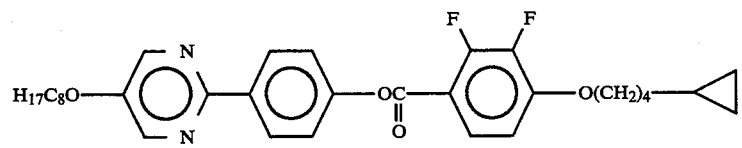

4-(5-octyloxypyrimidin-2-yl)phenyl
4-(4-cyclopropyl-butyloxy)-2,3-difluorobenzoate 4-(2-octyloxypyrimidin-5-yl)phenyl
4-(4-cyclopropyl-butyloxy)-2,3-difluorobenzoate

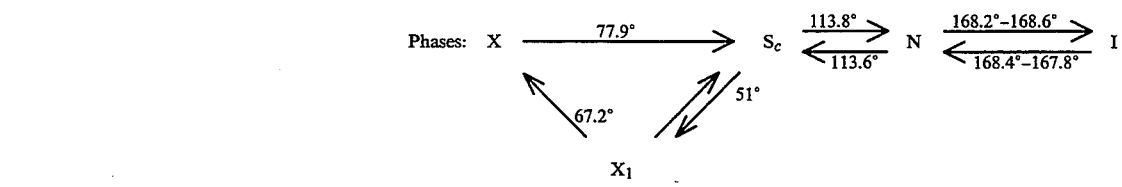

EXAMPLE 120

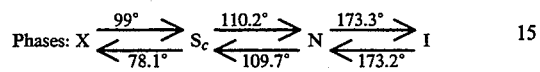

EXAMPLE 117

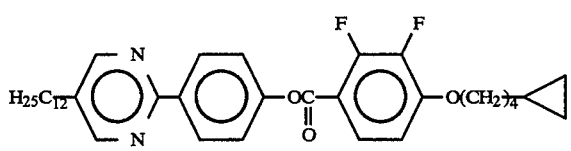

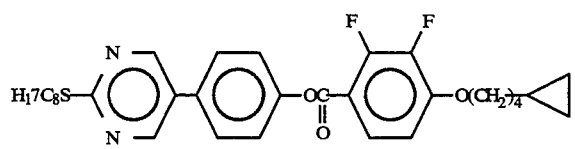

4-(2-octylthiopyrimidin-5-yl)phenyl
4-(4-cyclopropyl-butyloxy)-2,3-difluorobenzoate 4-(5-dodecylpyrimidin-2-yl)phenyl
4-(4-cyclopropyl-butyloxy)-2,3-difluorobenzoate

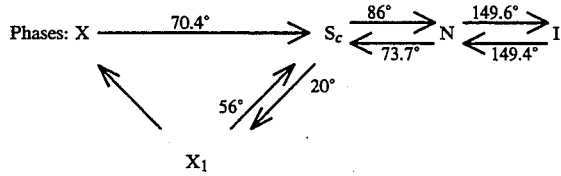

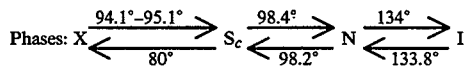

EXAMPLE 121

EXAMPLE 118

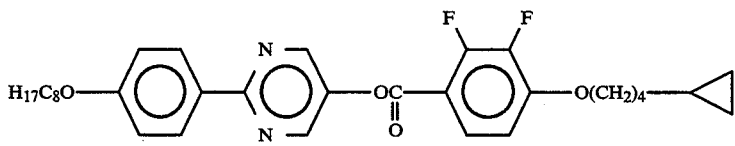

2-(4-octyloxyphenyl)pyrimidin-5-yl
4-(4-cyclopropyl-butyloxy)-2,3-difluorobenzoate

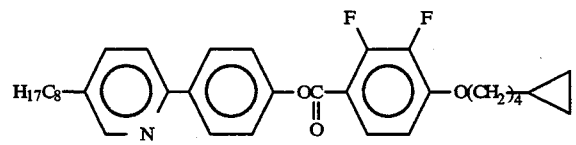

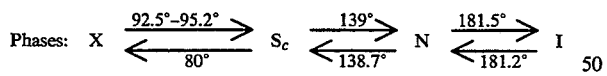

4-(5-octylpyridin-2-yl)phenyl
4-(4-cyclopropylbutyloxy)-2,3-difluorobenzoate

EXAMPLE 119

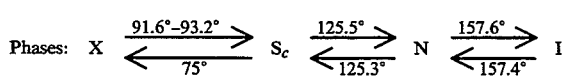

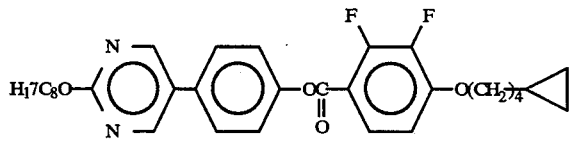

EXAMPLE 122

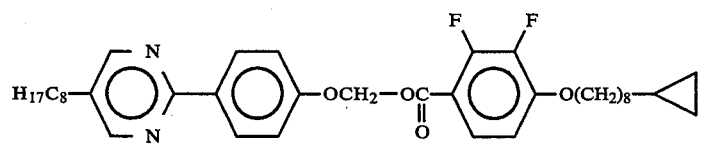

4-(5-octylpyrimidin-2-yl)phenyl
4-(8-cyclopropyl-octyloxy)-2,3-difluorobenzoate

Phases: X $\underset{78.4°}{\overset{78.5°-79.6°}{\rightleftarrows}}$ S$_c$ $\underset{81°}{\overset{81.1°}{\rightleftarrows}}$ N $\underset{85.6°}{\overset{85.8°}{\rightleftarrows}}$ I

EXAMPLE 123

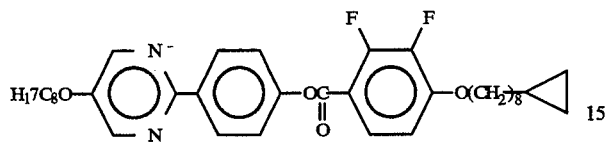

4-(5-octyloxypyrimidin-2-yl)phenyl
4-(8-cyclopropyl-octyloxy)-2,3-difluorobenzoate Phases: X $\underset{56.7°}{\overset{60.6°-64°}{\rightleftarrows}}$ S$_c$ $\underset{108°}{\overset{108.4°}{\rightleftarrows}}$ N $\underset{111.6°}{\overset{112°}{\rightleftarrows}}$ I

EXAMPLE 124

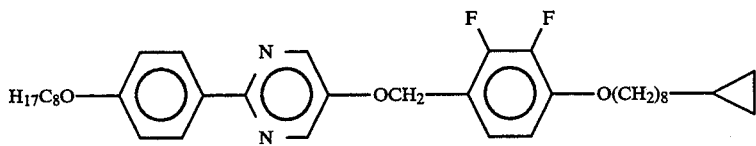

2-(4-octyloxyphenyl)pyrimidin-5-yl
4-(8-cyclopropyl-octyloxy)-2,3-difluorobenzoate

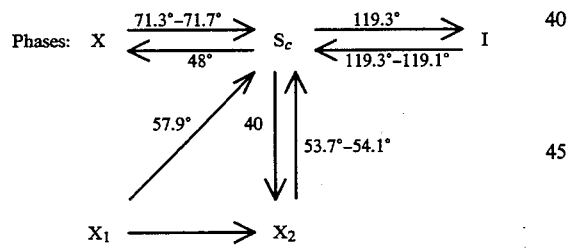

EXAMPLE 125

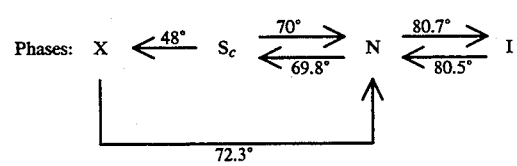

9-cyclopropylnonyl 4-(4-octyloxybenzoyloxy)phenyl
ether

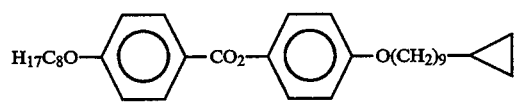

EXAMPLE 126

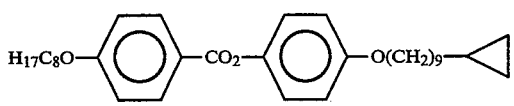

9-Cyclopropylnonyl 4-(4-octyloxybenzyloxy)benzoate

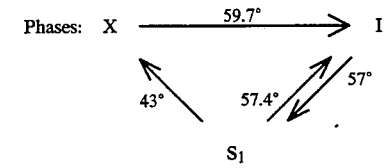

EXAMPLE 127

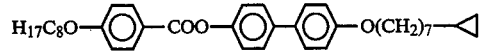

7-Cyclopropylheptyloxy
[4'-(4-octyloxybenzoyloxy)biphenyl-4-yl]

Phases: X $\underset{106°}{\overset{124.8°}{\rightleftarrows}}$ S$_c$ $\underset{156.1°}{\overset{156.3°}{\rightleftarrows}}$ N $\underset{187.4°-187.7°}{\overset{187.6°}{\rightleftarrows}}$ I

EXAMPLE 128

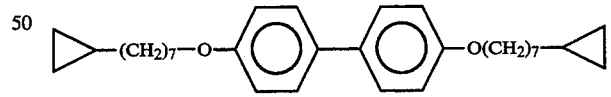

4,4'-Bis(7-cyclopropylheptyloxy)-1,1'-biphenyl

Phases: X $\underset{143.9°}{\overset{148.5°}{\rightleftarrows}}$ I

EXAMPLE 129

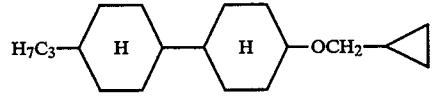

trans-4-(cyclopropylmethyl)oxycyclohexyl-trans-4-propyl-cyclohexane

Phases: X $\xrightarrow{31°}$ S$_x$ $\xrightarrow{56.8°}$ I
$\xleftarrow{0}$ $\xleftarrow{55}$ Extrapolated clear point ~5° C.

EXAMPLE 130

H$_7$C$_3$—[H]—[H]—O(CH$_2$)$_4$—◁ trans-4-(4-cyclopropylbutyl)oxycyclohexyl-trans-4-propyl-cyclohexane

Phases: X $\xrightarrow{45.4°}$ S$_x$ $\xrightarrow{56.3°}$ I
$\xleftarrow{30.4°}$ $\xleftarrow{55}$ Extrapolated clear point ~5° C.

EXAMPLE 131

F$_3$CO—⟨○⟩—[N pyrimidine]—O—CH$_2$—◁

5-Cyclooropylmethyloxy-2-(4-trifluoromethoxyphenyl)pyrimidine

Phases: X $\xrightarrow{97.2°}$ I
$\xleftarrow{89.9°}$

The clear point extrapolated from a mixture is 5° C.

EXAMPLE 132

F$_3$CO—⟨○⟩—[N pyrimidine]—O(CH$_2$)$_4$—◁

5-(4-Cyclopropylbutyl)oxy-2-(4-trifluoromethoxyphenyl)pyrimidine

Phases: X $\xrightarrow{71.1°}$ I
$\xleftarrow{68.3°}$

The clear point extrapolated from a mixtures is 25° C.

EXAMPLE 133

A binary mixture comprising:

65 mol-% of (4-hexyloxy)phenyl 4-octyloxybenzoate and 35 mol-% of (4-octyloxy)phenyl 4-(8-cyclopropyloctyloxy)-2,3-difluorobenzoate (Example 113) exhibited the following phase sequence:

Phases: X 34 S$_c$ 63 N 76 I

Comparison mixture:

| | |
|---|---|
| (4-Hexyloxy)phenyl 4-octyloxybenzoate | 65 mol % |
| (4-octyloxy)phenyl 4-decyloxy-2,3-difluorobenzoate | 35 mol % |
| Phases: X 37 S$_c$ 69 N 81 I | |

Comparison of the mixture shows that the mixture according to the invention had a melting point which was lower than that of the comparison mixture. The cyclopropyl component is therefore particularly suitable for practical application.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A liquid-crystalline cyclopropylalkyl-heterocyclic compound of the formula (I)

$$R^1(-A^1)_j(-M^1)_k(-A^2)_l(-M^2)_m(-A^3)_n-G\underset{H}{\overset{H}{\diagdown}}\underset{H}{\diagup}H \qquad (I)$$

in which

R$^1$ is straight-chain or branched (with or without an asymmetrical carbon atom) alkyl having 2 to 16 carbon atoms, it also being possible for one or two non-adjacent —CH$_2$— groups to be replaced by —O—, —S—, —CO—O— or —O—CO—, or R$^1$ is one of the following radicals $$R^2-\underset{Cl}{\overset{H}{\underset{|}{C}}}-CO-O, \quad R^2\underset{R^3}{\overset{O}{\diagup\!\!\diagdown}}-CO-O,$$

$$R^2\underset{R^3}{\diagup}\underset{O}{\overset{O}{\diagdown}}-CO-O, \quad R^2-\underset{F}{\overset{H}{\underset{|}{C}}}-O-CO \text{ or}$$

$$\underset{H}{\overset{H}{\diagdown}}\underset{H}{\diagup}G$$

A$^1$, A$^2$ and A$^3$ are identical or different 1,4-phenylene, trans-1,4-cyclohexylene, pyridazine-3,6-diyl, pyridine-2,5-diyl, pyrimidine-2,5-diyl or (1,3,4)-thiadiazole-2,5-diyl, M$^1$ and M$^2$ are identical or different CO—O, O—CO, CH$_2$—O or O—CH$_2$, G is straight-chain or branched alkylene having 1 to 16 carbon atoms, in which it is also possible for one or two non-adjacent —CH$_2$— groups to be replaced by —O—, —O—CO— or —CO—O—, R$^2$ and R$^3$ are H or straight-chain or branched alkyl having 1 to 16 carbon atoms and j, k, l, m and n are zero or 1, with the following provisos: a) j+l+n=2 or 3, and b) one of the groups A$^1$, A$^2$ and A$^3$ is not 1,4-phenylene or trans-1,4-cyclohexylene.

2. A liquid-crystalline cyclopropylalkyl-heterocyclic compound as claimed in claim 1, wherein, in the formula (I) , the (—A¹)ⱼ(—M¹)ₖ(—A²)ₗ(—M²)ₘ(—A³)ₙ— group is

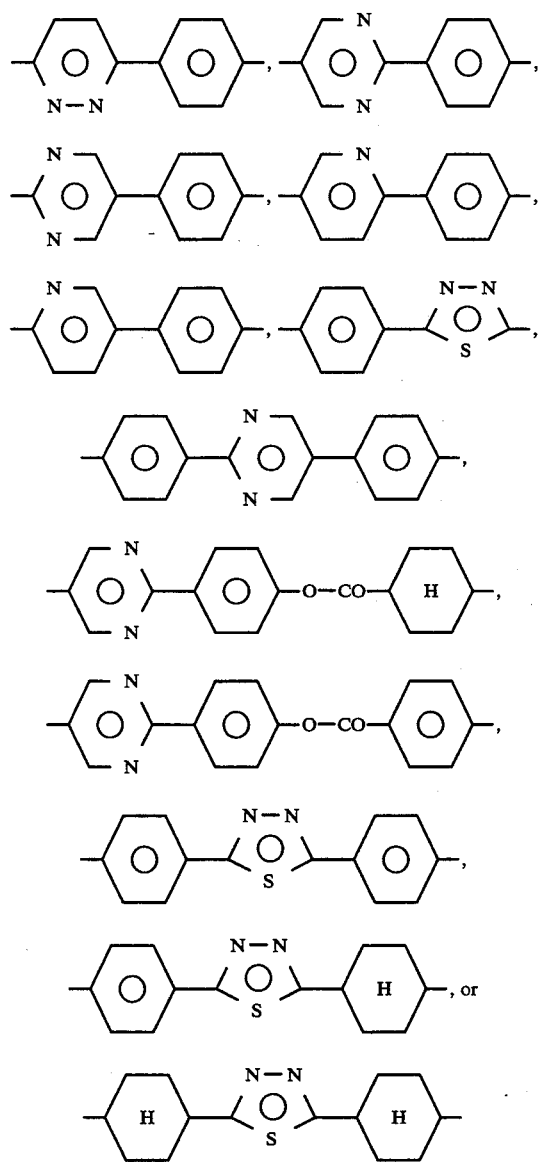

3. A nematic liquid-crystalline mixture containing at least one cyclopropylalkyl heterocyclic compound of the formula (I) as claimed in claim 1.

4. A nematic liquid-crystalline mixture containing at least one cyclopropylalkyl heterocyclic compound of the formula (I) as claimed in claim 2.

5. A smectic liquid-crystalline mixture containing at least one cyclopropylalkyl heterocyclic compound of the formula (I) as claimed in claim 1.

6. A smectic liquid-crystalline mixture containing at least one cyclopropylalkyl heterocyclic compound of the formula (I) as claimed in claim 2.

7. An electro-optical component containing a liquid-crystalline mixture as claimed in claim 3.

8. An electro-optical component contining a liquid-crystalline mixture as claimed in claim 4.

9. An electro-optical component contining a liquid-crystalline mixture as claimed in claim 5.

10. An electro-optical component contining a liquid-crystalline mixture as claimed in claim 6.

11. 5-(7-Cyclopropyl-heptyloxy)-2-pyrimidine.

12. A cyclopropylalkyl compound of the general formula (I)

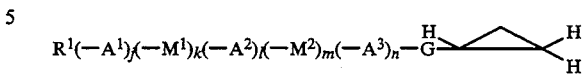

in which

R¹ is straight-chain or branched (with or without an asymmetric carbon atom) alkyl or alkenyl having 2 to 16 carbon atoms, it also being possible for one or two non-adjacent —CH₂— groups to be replaced by —O—, —S—, —CO—, —CO—O—, —O—CO— or —O—CO—O— and it also being possible for H to be replaced by F, or is one of the following radicals

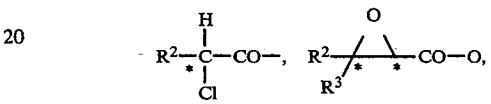

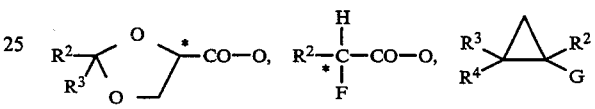

CN, OCF₃, OCF₂H, F or CH₃ A¹, A² and A³ are identical or different, unsubstituted or mono-or dihalo-substituted 1,4-phenylene, unsubstituted or 1- or 4-CN-substituted 1,4-cyclohexylene, pyridazine-3,6-diyl, pyridine-2,5-diyl, pyrimidine-2,5-diyl or (1,3,4,)-thiadiazole-2,5-diyl M¹ and M² are identical or different CO—O, O—CO, CH₂—O, O—CH₂, C≡C, CH₂—CH₂ or a single bond G is a straight-chain or branched alkylene having 1 to 16 carbon atoms in which it is also possible for one or two non-adjacent —CH₂— groups to be replaced by —O—, —O—CO—, —CO—O—, R², R³ and R⁴ are H or straight-chain or branched alkyl having 1 to 16 carbon atoms k and m are zero or 1 and j, l and n are zero, 1 or 2; and j+1+n is 2 or 3.

13. An embodiment as claimed in claim 12 wherein in the general formula (I), A¹, A² and A³ have the following meaning:

A¹, A² and A³ are identical or different mono-or difluoro-substituted 1,4-phenylene, unsubstituted 1,4-phenylene, 1,4-cyclohexylene, pyridine-2,5-diyl or pyrimidine-2,5-diyl.

14. A liquid-crystalline mixture containig at least one cyclopropylalkyl compound of the general formula (I) as claimed in claim 12.

15. An electrooptical component containing a liquid-crystalline mixture as claimed in claim 14.

16. A liquid-crystalline mixture as claimed in claim 15, wherein the liquid-crystalline mixture is nematic.

17. A liquid-crystalline mixture as claimed in claim 15, wherein the liquid-crystalline mixture is smectic.

18. A liquid-crystalline mixture as claimed in claim 15, wherein the liquid-crystalline mixture is chiral and smectic.

19. A liquid-crystalline mixture as claimed in claim 15, wherein the liquid-crystalline mixture is ferrolelectric.

* * * * *